US 6,686,164 B1

(12) United States Patent
Olsen et al.

(10) Patent No.: US 6,686,164 B1
(45) Date of Patent: Feb. 3, 2004

(54) LOW ALLERGENIC PROTEIN VARIANTS

(75) Inventors: Arne Agerlin Olsen, Kaplevej (DK); Erwin Lugo Roggen, Lyngby (DK); Steffen Ernst, Kobenhavn N (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/417,608

(22) Filed: Oct. 13, 1999

Related U.S. Application Data

(60) Provisional application No. 60/157,429, filed on Oct. 4, 1999, provisional application No. 60/111,386, filed on Dec. 8, 1998, and provisional application No. 60/107,165, filed on Nov. 5, 1998.

(30) Foreign Application Priority Data

Oct. 30, 1998 (DK) ........................................ 1998 01402
Nov. 25, 1998 (DK) ........................................ 1998 01645
Oct. 4, 1999 (DK) ........................................ 1999 01417

(51) Int. Cl.$^7$ .............................................. G01N 33/53
(52) U.S. Cl. ........... 435/7.1; 435/DIG. 4; 435/DIG. 15; 436/501; 436/513
(58) Field of Search ................... 435/7.1, DIG. 4, 435/DIG. 15; 436/501, 513

(56) References Cited

U.S. PATENT DOCUMENTS 6,251,620 B1 * 6/2001 Hatada et al. ................. 435/15

FOREIGN PATENT DOCUMENTS

| WO | WO 92/10755 | 6/1992 |
| WO | WO 93/11794 | 6/1993 |
| WO | WO 96/21016 | 7/1996 |
| WO | WO 99/38978 | 8/1999 |

OTHER PUBLICATIONS

Jespers et al., J. Mol. Biol. vol. 269 (1997) pp. 704–718.*
Williams et al., Journal of Immunological Methods, vol. 213, pp. 1–17 (1998).
Derwent Accession No. 1996–203147, Chugai Shoji KK, Japanese Abstract No. JP 08070866 (Mar. 19, 1996).

* cited by examiner

Primary Examiner—Bennett Celsa
(74) Attorney, Agent, or Firm—Elias J. Lambins

(57) ABSTRACT

The present invention relates to a method of selecting a protein variant having reduced immunogenicity as compared with the parent protein. This method includes the steps of screening a random peptide display package library with antibodies raised against any protein of interest, sequencing the amino acid sequence of the antibody binding peptides, or the DNA sequence encoding the antibody binding peptides, identifying epitope patterns of a protein by sequence alignment of the reactive peptide sequence, localization of epitope patterns on the primary 3-dimensional structure of the parent protein, defining an epitope area including amino acids situated within 5 Å from the epitope amino acids, and affecting antibody binding to the epitope, changing the localized epitope patterns, or amino acids defining the epitope area of the parent protein by genetic engineering mutations of a DNA sequence encoding the parent protein without impairing functionality of the protein using the emerging epitope database for eliminating amino acid substitutions creating new or duplicating existing epitope patterns, introducing the mutated DNA sequence into a suitable host, culturing the host and expressing the protein variant, and evaluating the immunogenicity of the protein variant using the parent protein as reference. The invention further relates to the protein variant and its use, as well as to a method for producing said protein variant.

21 Claims, 2 Drawing Sheets

Figure 1A:

Epitope: A172/A169 R170 A194 G193 N261
Pattern: A R > R > A > N
Antibody: IgG1 + IgE
Backbone: Savinase
Epitope area: P131, S132, A133, L135, E136, V139, A151, A152, S153, G161, S162, S166, Y167, P168, Y171, A174, A176, Q191, Y192, L196, R247, S259, T260, Y263, G264.

I165, N173, G195, L262,

Epitope: K251 R247 A174 N173
Pattern: R/K R F A N > E/D
Antibody: IgG1 + IgE
Backbone: Savinase
Epitope area: V139, N140, T143, L148, V149, A151, P168, A169, Y171, A172, M175, A176, D197, I198, N243, V244, Q245, I246, N248, H249, L250, N252, T253, A254, S265.

Epitope: T143 N173 N140 E136 L135
Pattern: S/T N N > E L
Antibody: IgG1
Backbone: Savinase
Epitope area: V10A, I107, A108, L111, E112, G115, S132, A133, T134, Q137, A138, V139, S141, A142, S144, R145, G146, V147, V149, Y167, P168, Y171, A172, A174, M175, N243, R247.

Epitope: S216 E219 Y220
Pattern: E Y > M
Antibody: IgG1
Backbone: Lipoprime
Epitope area: V2, L6, F10, A182, L185, T186, L193, Y194, R195, I196, T197, S214, H215, S217, P218, W221, I222, I235, V236, K237, I238, E239, G240, I241, A243, G246, N247, N248.

Black: epitope - Grey: epitope area

LOW ALLERGENIC PROTEIN VARIANTS

CROSS-REFERENCE TO RELATED APPLICATIONS

This application claims priority under 35 U.S.C. 119 of U.S. provisional application Nos. 60/107,165, 60/111,386 and 60/157,429 filed on Nov. 5, 1998, Dec. 8, 1998 and Oct. 4, 1999, respectively, and of Danish application nos. PA 1998 01402, PA 1998 01645 and PA 1999 01417 filed on Oct. 30, 1998, Nov. 25, 1998 and Oct. 4, 1999, respectively, the contents of which are fully incorporated herein by reference.

FIELD OF THE INVENTION

The present invention relates to a method of selecting a protein variant having reduced immunogenicity as compared with the parent protein, to the protein variant and use thereof, as well as to a method for producing the protein variant.

DESCRIPTION OF THE RELATED ART

An increasing number of proteins, including enzymes, are being produced industrially, for use in various industries, housekeeping and medicine. Being proteins they are likely to stimulate an immunological response in man and animals, including an allergic response.

In the present context the terms allergic response, allergy, allergenic and allergenicity are used according to their usual definitions, i.e. to describe the reaction due to immune responses wherein the antibody most often is IgE, less often $IgG_4$ and diseases due to this immune response. Allergic diseases include urticaria, hay-fever, asthma, and atopic dermatitis. They may even evolve into an anaphylactic shock.

Prevention of allergy in susceptible individuals is therefore a research area of great importance. Depending on the application, individuals get sensitized to the respective allergens by inhalation, direct contact with skin and eyes, or injection. The general mechanism behind an allergic response is divided in a sensitization phase and a symptomatic phase. The sensitization phase involves a first exposure of an individual to an allergen. This event activates specific T- and B-lymphocytes, and leads to the production of allergen specific immunoglobulin E (IgE) antibodies. These IgE antibodies eventually facilitate allergen capturing and presentation to T-lymphocytes at the onset of the symptomatic phase. This phase is initiated by a second exposure to the same or a resembling antigen. The specific IgE antibodies bind to the specific IgE receptors on mast cells and basophils, among others, and capture at the same time the allergen. The polyclonal nature of this process results in bridging and clustering of the IgE receptors, and subsequently in the activation of mast cells and basophils. This activation triggers the release of various chemical mediators involved in the early as well as late phase reactions of the symptomatic phase of allergy.

In the present context the antibodies are denoted as usual, i.e. immunoglobulin E is IgE etc.

Various attempts to reduce the immunogenicity of polypeptides and proteins have been conducted. It has been found that small changes in an epitope may affect the binding to an antibody. This may result in a reduced importance of such an epitope, maybe converting it from a high affinity to a low affinity epitope, or maybe even resulting in epitope loss, i.e. the epitope cannot sufficiently bind an antibody to elicit an immunogenic response.

In WO 92/10755 a method for modifying proteins to obtain less immunogenic variants is described. Randomly constructed protein variants, revealing a reduced binding of antibodies to the parent enzyme as compared to the parent enzyme itself, are selected for the measurement in animal models in terms of allergenicity. Finally, it is assessed whether reduction in immunogenicity is due to true elimination of an epitope or a reduction in affinity for antibodies. A drawback of this approach is its 'trial and error' character, which makes it a long and expensive process. Furthermore, no information is provided on the epitope as such, which implies that the information obtained for one protein cannot be applied on another, since the limited number of animals involved do not allow the identification of epitope patterns.

SUMMARY OF THE INVENTION

The present invention relates to a method of selecting a protein variant having reduced immunogenicity as compared with a parent protein, comprising the steps of:

screening a random peptide display package library with antibodies raised against any protein of interest;

sequencing the amino acid sequence of the antibody binding peptides, or the DNA sequence encoding the antibody binding peptides;

identifying epitope patterns by sequence alignment of the reactive peptide sequence;

localization of epitope patterns on the primary and 3-dimensional structure of the parent protein;

defining an epitope area including amino acids situated within 5 Å from the epitope amino acids;

changing the localized epitope patterns, or amino acids defining the epitope area of the parent protein by genetic engineering mutations of a DNA sequence encoding the parent protein without impairing functionality of the protein using the emerging epitope database for eliminating amino acid substitutions creating new or duplicating existing epitope patterns;

introducing the mutated DNA sequence into a suitable host, culturing the host and expressing the protein variant; and evaluating the immunogenicity of the protein variant using the parent protein as reference.

A second aspect of the present invention is a protein variant having reduced immunogenicity as compared with the parent protein. The amino acid sequence of the protein variant differs from the amino acid sequence of the parent protein with respect to at least one epitope pattern of the parent protein, such that the immunogenicity of the protein variant is reduced as compared with the immunogenicity of the parent protein. Preferably, the immunogenicity of the protein variant of a detergent enzyme is at least 10 times lower than the immunogenicity of the parent protein, preferably 25 times lower than the immunogenicity of the parent protein. In particular, for a protein variant used in personal care products the immunogenicity is preferably 100 times lower, more preferably 200 times lower, even more preferably 500 times lower than the immunogenicity of the parent protein. Furthermore, for food products and pharmaceuticals the immunogenicity is preferably 1000 times lower than the immunogenicity of the parent protein. Normally, a reduction of at most 50,000 times of the immunogenicity is sufficient for all purposes, of protein application. In this context the immunogenicity is assessed by the potential of the protein to evoke an antibody response with focus in IgE responses.

Reduction of immunogenicity in the context above is defined by the differences observed among the kinetics obtained with various doses of the parent protein, as compared with the variants under investigation. In the present study the effect of epitope guided protein engineering is assessed by kinetic studies using a single dose of the protein under investigation.

The immunogenicity of the protein variant is measured in animal tests, wherein the animals are immunized with the protein variant and the immune response is measured. By the present invention the immunogenicity is reduced at least 100 times as compared with the immunogenicity of the parent protein, preferably 200 times reduced, more preferably 500 times.

However, the present inventors have demonstrated that the performance in a competitive ELISA correlates closely to the immunogenic responses measured in animal tests.

To obtain a useful reduction of the immunogenicity or a protein, the immunogenicity of the protein variant must be reduced to at least below 75%, preferably below 50% of the immunogenicity of the parent protein as measured by the performance in competitive ELISA, given the value for immunogenicity of the parent protein is set to 100%. When the immunogenicity is below 50% of the immunogenicity of the parent protein, the protein variant is practically non-allergenic, that is, no IgE response will be measurable in animal tests.

A further aspect of the present invention is a composition comprising a protein variant as defined above, as well as the use of the composition for industrial application, such as the production of a formulation for personal care products (for example shampoo; soap; skin, hand and face lotions; skin, hand and face cremes; hair dyes; toothpaste), food (for example in the baking industry), detergents and for the production of pharmaceuticals.

Yet another aspect is a DNA molecule encoding a protein variant as defined above.

Further aspects are a vector comprising a DNA molecule as described above as well a host cell comprising said DNA molecule.

Another aspect is a method of producing a protein variant having reduced immunogenicity as compared with the parent protein as defined above.

BRIEF DESCRIPTION OF THE DRAWINGS

FIG. 1 shows the 3D-structure of Savinase and Lipoprime with the location of 4 epitopes and their corresponding epitope areas.

FIG. 2 shows competitive ELISA data.

DETAILED DESCRIPTION OF THE INVENTION

By the term a protein variant having reduced immunogenicity as compared with the parent protein is meant a protein variant which differs from the parent protein in one or more amino acids whereby the immunogenicity of the variant is reduced. The reduction of immunogenicity may be confirmed by testing the ability of the protein variant to elicit an IgE response.

In the present context the term protein is intended to cover oligopeptides, polypeptides as well as proteins as such.

The display package can be, for example, derived from bacterial viruses. A preferred display package may be a phage display system. In a phage display system, a sequence encoding a desired amino acid sequence is incorporated into a phage gene coding for a protein displayed on the surface of the phage. Thus, the phage will make and display the hybrid protein on its surface, where it can interact with specific target agents. Given that each phage was given one specific sequence of a determined length, an average phage display library can express $10^8$–$10^{12}$ different random sequences. The incorporated sequence being an epitope, the target agent could for example be an epitope-specific antibody. Thus, it is possible to select specific phages from the bulk of a large number of phages, each expressing their one hybrid protein.

In a preferred embodiment, the length of the incorporated peptide is 9 amino acids.

The antibodies used for reacting with the display package are preferably IgE antibodies to ensure that the epitopes identified are IgE epitopes, i.e. epitopes inducing and binding IgE. In a preferred embodiment the antibodies are polyclonal antibodies, optionally monospecific antibodies.

By the term "monospecific antibodies" is meant polyclonal antibodies isolated according to their specificity for a certain epitope pattern. Such monospecific antibodies will only bind to one epitope pattern, but they will most often be produced by a number of antibody producing cells, recognizing similar epitope patterns, thereby being polyclonal.

For the purpose of the present invention polyclonal antibodies are preferred in order to obtain a broader knowledge about the epitopes of a protein.

Furthermore, the antibody IgE is normally found in very low concentration in serum. Normal serum IgE antibody concentration is below $10^{-3}$ g/l, as compared with normal IgG concentration of 12 g/l. Accordingly, in practice it is very difficult to obtain a monoclonal antibody library covering all possible epitope patterns on an intact protein. However, after affinity purification of IgE antibodies from serum raised against the protein it is possible to obtain polyclonal or monospecific IgE antibodies suitable for the present invention.

In general, the parts of a protein recognized and bound by antibodies, i.e. the epitopes, may be linear or structural. By linear epitope is meant that the amino acids of the epitope are placed in sequence in the primary protein structure. Structural epitopes differ from linear epitopes in that they do not appear until after the three-dimensional structure of the protein is formed. A structural epitope is comprised of amino acid sequences from different parts of the primary structure of the protein, only brought together after the folding of the protein sequence forming the secondary and/or tertiary structures, thereby forming a contiguous epitope surface. By the term an epitope pattern or epitope motif is meant the epitope constituting surface of the protein independent of whether the epitope is linear or structural. Some of the epitopes are more important (high affinity epitopes) than other (low affinity) with respect to binding affinity.

A protein may have more than one epitope. From theoretical models it is estimated that proteins with a molecular size of 30.000 Daltons may carry up to 6 epitope areas on its surface. The total number of actual epitopes however must be much higher. For example, a 9-mer amino acid sequence provides binding to at least 5 different monoclonal antibodies, considering a 5-mer as the minimum epitope size.

It has been found that some of the IgG1 antibody binding epitopes do not bind IgE antibodies, and vice versa. Accordingly, the epitopes may be more or less specific for specific antibody classes.

More than 80% of the IgE epitopes are considered structural epitopes, whereby the epitopes can be destroyed during heating of the protein, the use of detergents or other procedures implying denaturation. This percentage may vary for different proteins. Consequently, the use of overlapping peptide fragments covering the entire protein for the identification of IgE epitopes is not applicable. However, the present inventors find that by the use of small amino acid sequences in a display package it is possible to identify epitope patterns of linear as well as structural epitopes, due to the random character of the sequence of the expressed oligopeptides.

The peptides presented on the display packages and identified by the antibodies are then sequenced, or their sequence is derived by translation of the corresponding DNA sequence. Both sequences are obtained by techniques known to the person skilled in the art of genetic engineering.

The epitope patterns are identified by comparison of the sequences of the peptides bound by the antibody. Subsequently, the identified patterns are localized on the primary as well as 3-dimensional structure of the parent protein, and eventually on any protein of interest. Within the epitope patterns some amino acids may be highly conservative, called anchor amino acids. The anchor amino acids will be recurring in all the peptides bound by monospecific antibodies, and define the epitope pattern.

It is of great importance that the amino acid sequence of the peptides presented by the display packages is long enough to present a significant part of the epitope to be identified. In a preferred embodiment of the invention the peptides of the peptide display package library are oligopeptides having from 5 to 25 amino acids, preferably at least 8 amino acids, such as 9 amino acids. The complexity of the package library, which is the number of display packages to get a suitable representation of all possible epitopes, may be calculated on basis of the estimated length of the epitope to be identified, such as by the formula below.

Number of packages=$20^n$, wherein n is the number of residues in the epitope.

Typical actions required for the construction of a model structure are: alignment of homologous sequences for which 3-dimensional structures exist, definition of Structurally Conserved Regions (SCRs), assignment of coordinates to SCRs, search for structural fragments/loops in structure databases to replace Variable Regions, assignment of coordinates to these regions, and structural refinement by energy minimization. Regions containing large inserts ($\geq 3$ residues) relative to the known 3-dimensional structures are known to be quite difficult to model, and structural predictions must be considered with care.

Having obtained the 3-dimensional structure of the polypeptide in question, or a model of the structure based on homology to known structures, this structure serves as an essential prerequisite for the fulfillment of the method described below.

When the epitope(s) have been identified, a protein variant exhibiting a reduced immunogenicity may be produced by changing the identified epitope pattern of the parent protein by mutation and/or genetic engineering of a DNA sequence encoding the parent protein.

The epitope identified may be changed by substituting at least one amino acid of the epitope area. In a preferred embodiment at least one anchor amino acid is changed. The change will often be substituting to an amino acid of different size, hydrophilicity, and/or polarity, such as a small amino acid versus a large amino acid, a hydrophilic amino acid versus a hydrophobic amino acid, a polar amino acid versus a non-polar amino acid and a basic versus an acidic amino acid.

Other changes may be the addition or deletion of at least one amino acid of the epitope, preferably deleting an anchor amino acid. Furthermore, an epitope pattern may be changed by substituting some amino acids, and deleting/adding others.

Substitutions/Insertions for Subsequent Covalent Conjugation to Amino Acids in the Epitope Area Which amino acids to substitute and/or insert depends in principle on the coupling chemistry to be applied. The chemistry for preparation of covalent bioconjugates can be found in "Bioconjugate Techniques", Hermanson, G. T. (1996), Academic Press Inc. which is hereby incorporated as reference.

It is preferred to conjugates activated polymers to amino acids in the epitope area.

It is preferred to make conservative substitutions in the polypeptide when the polypeptide has to be conjugated, as conservative substitutions secure that the impact of the substitution on the polypeptide structure is limited.

In the case of providing additional amino groups this may be done by substitution of Arginine to Lysine, both residues being positively charged, but only the Lysine having a free amino group suitable as an attachment group.

In the case of providing additional carboxylic acid groups the conservative substitution may for instance be an Asparagine to Aspartic acid or Glutamine to Glutamic acid substitution. These residues resemble each other in size and shape, except from the carboxylic groups being present on the acidic residues.

In the case of providing SH-groups the conservative substitution may be done by substitution of Threonine or Serine to Cysteine.

Activation of Polymers

If the polymeric molecules to be conjugated with the polypeptide in question are not active it must be activated by the use of a suitable technique. It is also contemplated according to the invention to couple the polymeric molecules to the polypeptide through a linker. Suitable linkers are well-known to the skilled person.

Methods and chemistry for activation of polymeric molecules as well as for conjugation of polypeptides are intensively described in the literature. Commonly used methods for activation of insoluble polymers include activation of functional groups with cyanogen bromide, periodate, glutaraldehyde, biepoxides, epichlorohydrin, divinylsulfone, carbodiimide, sulfonyl halides, trichlorotriazine etc. (see R. F. Taylor, (1991), "Protein immobilisation. Fundamental and applications", Marcel Dekker, NY.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymers but are also applicable to activation of soluble polymers e.g. periodate, trichlorotriazine, sulfonylhalides, divinylsulfone, carbodiimide etc. The functional groups being amino, hydroxyl, thiol, carboxyl, aldehyde or sulfydryl on the polymer and the chosen attachment group on the protein must be considered in choosing the activation and conjugation chemistry which normally consist of i) activation of polymer, ii) conjugation, and iii) blocking of residual active groups.

In the following a number of suitable polymer activation methods will be described shortly. However, it is to be understood that other methods also may be used.

Coupling polymeric molecules to the free acid groups of polypeptides may be performed with the aid of diimide and for example amino-PEG or hydrazino-PEG (Pollak et al., (1976), J. Amr. Chem. Soc., 98, 289–291) or diazoacetate/amide (Wong et al., (1992), "Chemistry of Protein Conjugation and Crosslinking", CRC Press).

Coupling polymeric molecules to hydroxy groups are generally very difficult as it must be performed in water. Usually hydrolysis predominates over reaction with hydroxyl groups.

Coupling polymeric molecules to free sulfhydryl groups can be reached with special groups like maleimido or the ortho-pyridyl disulfide. Also vinylsulfone (U.S. Pat. No. 5,414,135, (1995), Snow et al.) has a preference for sulfhydryl groups but is not as selective as the other mentioned.

Accessible Arginine residues in the polypeptide chain may be targeted by groups comprising two vicinal carbonyl groups.

Techniques involving coupling electrophilically activated PEGs to the amino groups of Lysines may also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135; Mosbach, K., Ed.; Academic Press: Orlando, pp. 65–79; Scouten et al., (1987), Methods in Enzymology vol. 135, Mosbach, K., Ed., Academic Press: Orlando, 1987; pp 79–84; Crossland et al., (1971), J. Amr. Chem. Soc. 1971, 93, pp. 4217–4219), mesylates (Harris, (1985), supra; Harris et al., (1984), J. Polym. Sci. Polym. Chem. Ed. 22, pp 341–352), aryl sulfonates like tosylates, and para-nitrobenzene sulfonates can be used.

Organic sulfonyl chlorides, e.g. Tresyl chloride, effectively converts hydroxy groups in a number of polymers, e.g. PEG, into good leaving groups (sulfonates) that, when reacted with nucleophiles like amino groups in polypeptides allow stable linkages to be formed between polymer and polypeptide. In addition to high conjugation yields, the reaction conditions are in general mild (neutral or slightly alkaline pH, to avoid denaturation and little or no disruption of activity), and satisfy the non-destructive requirements to the polypeptide.

Tosylate is more reactive than the mesylate but also more unstable decomposing into PEG, dioxane, and sulfonic acid (Zalipsky, (1995), Bioconjugate Chem., 6, 150–165). Epoxides may also be used for creating amine bonds but are much less reactive than the above mentioned groups.

Converting PEG into a chloroformate with phosgene gives rise to carbamate linkages to Lysines. This theme can be played, in many variants substituting the chlorine with N-hydroxy succinimide (U.S. Pat. No. 5,122,614, (1992); Zalipsky et al., (1992)., Biotechnol. Appl. Biochem., 15, p. 100–114; Monfardini et al., (1995), Bioconjugate Chem., 6, 62–69, with imidazole (Allen et al., (1991), Carbohydr. Res., 213, pp 309–319), with para-nitrophenol, DMAP (EP 632 082 A1, (1993), Looze, Y.) etc. The derivatives are usually made by reacting the chloroformate with the desired leaving group. All these groups give rise to carbamate linkages to the peptide.

Furthermore, isocyanates and isothiocyanates may be employed yielding ureas and thioureas, respectively.

Amides may be obtained from PEG acids using the same leaving groups as mentioned above and cyclic imid thrones (U.S. Pat. No. 5,349,001, (1994), Greenwald et al.). The reactivity of these compounds are very high but may make the hydrolysis too fast.

PEG succinate made from reaction with succinic anhydride can also be used. The hereby comprised ester group make the conjugate much more susceptible to hydrolysis (U.S. Pat. No. 5,122,614, (1992), Zalipsky). This group may be activated with N-hydroxy succinimide.

Furthermore, a special linker can be introduced. The oldest being cyanuric chloride (Abuchowski et al., (1977), J. Biol. Chem., 252, 3578–3581; U.S. Pat. No. 4,179,337, (1979), Davis et al.; Shafer et al., (1986), J. Polym. Sci. Polym. Chem. Ed., 24, 375–378.

Coupling of PEG to an aromatic amine followed by diazotation yields a very reactive diazonium salt which in situ can be reacted with a peptide. An amide linkage may also be obtained by reacting an azlactone derivative of PEG (U.S. Pat. No. 5,321,095, (1994), Greenwald, R. B.) thus introducing an additional amide linkage.

As some peptides do not comprise many Lysines it may be advantageous to attach more than one PEG to the same Lysine. This can be done e.g. by the use of 1,3-diamino-2-propanol.

PEGs may also be attached to the amino-groups of the enzyme with carbamate linkages (WO 95/11924, Greenwald et al.). Lysine residues may also be used as the backbone.

The coupling technique used in the examples is the N-succinimidyl carbonate conjugation technique described in WO 90/13590 (Enzon).

Conjugation of polymeric molecules to substitution and/or insertion variants for covalent conjugation.

Only substitutions and/or insertions which provide polypeptide-conjugates with reduced immune response when evaluated in animal models are within the concept of the present invention.

The mutation(s) performed may be performed by standard techniques well known in the art, such as site-directed mutagenesis (see, e.g., Sambrook et al. (1989), Molecular Cloning. A Laboratory Manual, Cold Spring Harbor, N.Y.

A general description of nucleotide substitution can be found in e.g. Ford et al., 1991, Protein Expression and Purification 2, p. 95–107.

The above-mentioned DNA sequence may be produced by any suitable technique known to the person skilled in the art of genetic engineering. The DNA sequence is introduced into a suitable host, which is cultured and the protein variant is expressed.

The risk linked to protein engineering in order to eliminate epitopes, is that new epitopes are made, or existing epitopes are duplicated. To reduce this risk, the planned mutations at a given position were put on the 3-dimensional structure of the protein of interest, and emerging amino acid constellation was run through the epitope database. This invention evidences that the risk mutations can be identified by this procedure, thereby reducing the number of possible mutations per position.

It is a well established fact that amino acids surrounding B- and T-cell epitopes can affect binding of the antibodies or T-cell receptors to the ligand. To anticipate to this possibility, an epitope area was defined on the 3-dimensional structure of the protein of interest.

It is of great importance that the changes of the epitope(s) do not interfere with or impair the functionality of the parent protein. Accordingly, the changes must not significantly change the secondary structure of the protein. By computer modeling it is possible to assess whether changes made in one or more epitopes will interfere substantially with the functionality of the protein. By the term "functionality" is meant the normal function of the protein, such as the enzymatic activity, thermal stability, chemical stability, and glycosylation.

In a preferred embodiment of the invention, more than one amino acid residue is substituted, added or deleted, these amino acids preferably being located in different epitope areas. In that case, it may be difficult to assess a priori how well the functionality of the protein is maintained while antigenicity, immunogenicity and/or allergenicity is reduced, especially since the possible number of combinations of mutations becomes very large, even for a small number of mutations. In that case, it will be an advantage to establish a library of diversified mutants each having one or more changed amino acids introduced and selecting those variants which show good retention of function and at the same time a good reduction in antigenicity. In the case of protease, this can be tested by assaying the secreted variants for enzyme activity and for antigen binding (e.g. by competitive ELISA) (as described below in the experimental section). The scope of these embodiments of the invention is by no means limited to protease, which serves only to provide an example. A diversified library can be established by a range of techniques known to the person skilled in the art (Reetz M T; Jaeger K E, in *Biocatalysis—from Discovery to Application* edited by Fessner W D, Vol. 200, pp. 31–57 (1999); Stemmer, Nature, vol. 370, p.389–391, 1994; Zhao and Arnold, Proc. Natl. Acad. Sci., USA, vol. 94, pp. 7997–8000, 1997; or Yano et al., Proc. Natl. Acad. Sci., USA, vol. 95, pp 5511–5515, 1998). In a more preferable embodiment, substitutions are found by a method comprising the following steps: 1) a range of substitutions, additions, and/or deletions are listed encompassing several epitope areas, 2) a library is designed which introduces a randomized subset of these changes in the amino acid sequence into the target gene, e.g. by random mutagenesis, 3) the library is expressed, and preferred variants are selected. In a most preferred embodiment, this method is supplemented with additional rounds of screening and/or family shuffling of hits from the first round of screening (J. E. Ness, et al, Nature Biotechnology, vol. 17, pp. 893–896, 1999) and/or combination with other methods of reducing allergenicity by genetic means (such as that disclosed in WO 92/10755).

Another object of the present invention is a protein variant having reduced immunogenicity as compared to the parent protein, wherein the amino acid sequence of the protein variant differs from the amino acid sequence of the parent protein with respect to one or more amino acids of the parent protein, such that the immunogenicity of the protein variant is reduced compared to the immunogenicity of the parent protein.

The reduced immunogenicity may be confirmed by testing the ability of the protein variant to elicit an IgE response in animal testing. The test animal may be any suitable animal. Preferably, the test animal may be rats, such as Brown Norway rats, or mice, such as the strains BaBallb/c, BDF1 and CB6F1.

The animal testing may be carried out as described in the following.

The following is a description of the processes involved in the determination of the immunogenicity in test animals. In the example the test animals are Brown Norway rats.

Materials

Molecules of a Protein Variant

ELISA Reagents

Horse Radish Peroxidase labelled pig anti-rabbit-Ig (Dako, DK, P217, dilution 1:1000).

Rat anti-mouse IgE (Serotec MCA419; dilution 1:100).

Mouse anti-rat IgE (Serotec MCA193; dilution 1:200).

Biotin-labelled mouse anti-rat IgG1 monoclonal antibody (Zymed 03–9140; dilution 1:1000).

Biotin-labelled rat anti-mouse IgG1 monoclonal antibody (Serotec MCA336B; dilution 1:2000).

Streptavidin-horse radish peroxidase (Kirkegård & Perry 14-30-00; dilution 1:1000).

Buffers and Solutions

PBS (pH 7.2 (1 liter))

| | |
|---|---|
| NaCl | 8.00 g |
| KCl | 0.20 g |
| $K_2HPO_4$ | 1.04 g |
| $KH_2PO_4$ | 0.32 g |

Washing buffer PBS, 0.05% (v/v) Tween 20

Blocking buffer PBS, 2% (wt/v) Skim Milk powder

Dilution buffer PBS, 0.05% (v/v) Tween 20, 0.5% (wt/v) Skim Milk powder

Citrate buffer (0.1M, pH 5.0–5.2 (1 liter))

| | |
|---|---|
| NaCitrate | 20.60 g |
| Citric acid | 6.30 g |

Stop-solution (DMG-buffer)

Sodium Borate, borax (Sigma)

3,3-Dimethyl glutaric acid (Sigma)

$CaCl_2$ (Sigma)

Tween 20: Poly oxyethylene sorbitan mono laurate (Merck cat no. 822184)

N-Hydroxy succinimide (Fluka art. 56480))

Phosgene (Fluka art. 79380)

Lactose (Merck 7656)

PMSF (phenyl methyl sulfonyl flouride) from Sigma

Succinyl-Alanine-Alanine-Proline-Phenylalanine-paranitro-anilide (Suc-AAPF-pNP) (SEQ ID NO: 87) Sigma no. S-7388, Mw 624.6 g/mol.

mPEG (Fluka)

Coloring Substrate

OPD: o-phenylene-diamine, (Kementec cat no. 4260)

Test Animals

Female Balb/C mice (about 20 grams) pruchased from Bomholdtgaard Ry, Denmark.

Equipment

XCEL II (Novex)

ELISA reader (UVmax, Molecular Devices)

HPLC (Waters)

PFLC (Pharmacia)

Superdex-75 column, Mono-Q, Mono S from Pharmacia, SW.

SLT: Fotometer from SLT LabInstruments

Size-exclusion chromatograph (Spherogel TSK-G2000 SW).

Size-exclusion chromatograph (Superdex 200, Pharmacia, SW)

Amicon Cell

Methods

Subcutanuous (SC) Immunisation of Balb/C Mice

For SC administration of molecules 0.05 ml of a solution of the molecules is deposited.

The test animals are Balb/C mice in groups of 10. Weight at time of start is more than 20 grams.

ELISA Procedure to Determine Relative Concentrations of IgE Antibodies in Balb/C Mice A three layer sandwich ELISA is used to determine relative concentrations of specific IgE serum anti-bodies.
1. Coat the ELISA-plate with 10 mg rat anti-mouse IgE Buffer 1 (50 microL/well). Incubate over night at 4° C.
2. Empty the plates and block with Blocking buffer for at least ½ hour at room temperature (200 microL/well). Shake gently. Wash the plates 3 times with Washing Buffer.
3. Incubate with mouse sera (50 microL/well), starting from undiluted and continue with 2-fold dilutions. Keep some wells free for buffer 4 only (blanks). Incubate for 30 minutes at room temperature. Shake gently. Wash the plates 3 times in washing Buffer.
4. Dilute the enzyme in Dilution buffer to the appropriate protein concentration. Incubate 50 microL/well for 30 minutes at room temperature. Shake gently. Wash the plates 3 times in Washing Buffer.
5. Dilute specific polyclonal anti-enzyme antiserum serum (pIg) for detecting bound antibody in Dilution buffer. Incubate 50 microl/well for 30 minutes at room temperature. Shake gently. Wash the plates 3 times in Washing Buffer.
6. Dilute Horseradish Peroxidase-conjugated anti-pIg-antibody in Dilution buffer. Incubate 50 microL/well at room temperature for 30 minutes. Shake gently. Wash the plates 3 times in Washing Buffer.
7. Mix 0.6 mg ODP/ml+0.4 microL $H_2O_2$/ml in substrate Buffer. Make the solution just before use. Incubate for 10 minutes. 50 microL/well.
8. To stop the reaction, add 50 microL Stop Solution/well.
9. Read the plates at 492 nm with 620 nm as reference.

Determination of the Molecular Weight

Electrophoretic separation of proteins is performed by standard methods using 4–20% gradient SDS polyacrylamide gels (Novex). Proteins were detected by silver staining. The molecular weight was measured relatively to the mobility of Mark-12® wide range molecular weight standards from Novex.

Protease Activity

Analysis with Suc-Ala-Ala-Pro-Phe-pNa (SEQ ID NO: 87)

Proteases cleave the bond between the peptide and p-nitroaniline to give a visible yellow colour absorbing at 405 nm.

Buffer: e.g. Britton and Robinson buffer pH 8.3.

Substrate: 100 mg suc-AAPF-pNa (SEQ ID NO: 87) is dissolved into 1 ml dimethyl sulfoxide (DMSO). 100 µl of this is diluted into 10 ml with Britton and Robinson buffer.

Analysis

The substrate and protease solution is mixed and the absorbance is monitored at 405 nm as a function of time and $ABS_{405\ nm}$/min. The temperature should be controlled (20–50° C. depending on protease). This is a measure of the protease activity in the sample.

The parent protein may be any protein, such as any naturally occurring protein as well as any variant thereof, optionally a variant in order to obtain a better functionality of the protein in question.

Pharmaceutical Polypeptides

The term "pharmaceutical polypeptides" is defined, as polypeptides, including peptides, such as peptide hormones, proteins and/or enzymes, being physiologically active when introduced into the circulatory system of the body of humans and/or animals.

Pharmaceutical polypeptides are potentially immunogenic as they are introduced into the circulatory system.

Examples of "pharmaceutical polypeptides" contemplated according to the invention include insulin, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, antidiuretic hormones, thyroid stimulating hormone, relaxin, interferon, thrombopoietin (TPO) and prolactin.

However, the proteins are preferably to be used in industry, housekeeping and/or medicine, such as proteins used in personal care products (for example shampoo; soap; skin, hand and face lotions; skin, hand and face cremes; hair dyes; toothpaste), food (for example in the baking industry), detergents and pharmaceuticals.

In one embodiment of the invention the protein is an enzyme, such as glycosyl hydrolases, carbohydrases, peroxidases, proteases, lipases, phytases, polysaccharide lyases, oxidoreductases, transglutaminases and glycoseisomerases, in particular the following.

Parent Proteases

Parent proteases (i.e. enzymes classified under the Enzyme Classification number E.C. 3.4 in accordance with the Recommendations (1992) of the International Union of Biochemistry and Molecular Biology (IUBMB)) include proteases within this group.

Examples include proteases selected from those classified under the Enzyme Classification (E.C.) numbers:

3.4.11 (i.e. so-called aminopeptidases), including 3.4.11.5 (Prolyl aminopeptidase), 3.4.11.9 (X-pro aminopeptidase), 3.4.11.10 (Bacterial leucyl aminopeptidase), 3.4.11.12 (Thermophilic aminopeptidase), 3.4.11.15 (Lysyl aminopeptidase), 3.4.11.17 (Tryptophanyl aminopeptidase), 3.4.11.18 (Methionyl aminopeptidase);

3.4.21 (i.e. so-called serine endopeptidases), including 3.4.21.1 (Chymotrypsin), 3.4.21.4 (Trypsin), 3.4.21.25 (Cucumisin), 3.4.21.32 (Brachyurin), 3.4.21.48 (Cerevisin) and 3.4.21.62 (Subtilisin);

3.4.22 (i.e. so-called cysteine endopeptidases), including 3.4.22.2 (Papain), 3.4.22.3 (Ficain), 3.4.22.6 (Chymopapain), 3.4.22.7 (Asclepain), 3.4.22.14 (Actinidain), 3.4.22.30 (Caricain) and 3.4.22.31 (Ananain);

3.4.23 (i.e. so-called aspartic endopeptidases), including 3.4.23.1 (Pepsin A), 3.4.23.18 (Aspergillopepsin I), 3.4.23.20 (Penicillopepsin) and 3.4.23.25 (Saccharopepsin); and 3.4.24 (i.e. so-called metalloendopeptidases), including 3.4.24.28 (Bacillolysin).

Examples of relevant subtilisins comprise subtilisin BPN', subtilisin amylosacchariticus, subtilisin 168, subtilisin mesentericopeptidase, subtilisin Carlsberg, subtilisin DY, subtilisin 309, subtilisin 147, thermitase, aqualysin, Bacillus PB92 protease, proteinase K, Protease TW7, and Protease TW3.

Specific examples of such readily available commercial proteases include Esperase®, Alcalase®, Neutrase®, Dyrazym®, Savinase®, Pyrase®, Pancreatic Trypsin NOVO (PTN), Bio-Feed™ Pro, Clear-Lens Pro (all enzymes available from Novo Nordisk A/S).

Examples of other commercial proteases include Maxtase®, Maxacal®, Maxapem® marketed by Gist-Brocades N.V., Opticlean® marketed by Solvay et Cie. and Purafect® marketed by Genencor International.

It is to be understood that also protease variants are contemplated as the parent protease. Examples of such protease variants are disclosed in EP 130 756 (Genentech), EP 214 435 (Henkel), WO 87/04461 (Amgen), WO 87/05050 (Genex), EP 251 446 (Genencor), EP 260 105 (Genencor), Thomas et al., (1985), Nature. 318, p. 375–376, Thomas et al., (1987), J. Mol. Biol., 193., pp. 803–813, Russel et al., (1987), Nature, 328, p. 496–500, WO 88/08028 (Genex), WO 88/08033 (Amgen), WO 89/06279 (Novo Nordisk A/S), WO 91/00345 (Novo Nordisk A/S), EP 525 610 (Solvay) and WO 94/02618 (Gist-Brocades N.V.).

The activity of proteases can be determined as described in "Methods of Enzymatic Analysis", third edition, 1984, Verlag Chemie, Weinheim, vol. 5.

Parent Lipases

Parent lipases (i.e. enzymes classified under the Enzyme Classification number E.C. 3.1.1 (Carboxylic Ester Hydrolases) in accordance with the Recommendations (1992) of the International Union of Biochemistry and Molecular Biology (IUBMB)) include lipases within this group.

Examples include lipases selected from those classified under the Enzyme Classification (E.C.) numbers:

3.1.1 (i.e. so-called Carboxylic Ester Hydrolases), including (3.1.1.3) Triacylglycerol lipases, (3.1.1.4.) Phosphorlipase $A_2$.

Examples of lipases include lipases derived from the following microorganisms. The indicated patent publications are incorporated herein by reference:

Humicola, e.g. *H. brevispora, H. lanuginosa, H. brevis* var. *thermoidea* and *H. insolens* (U.S. Pat. No. 4,810,414).

Pseudomonas, e.g. *Ps. fragi, Ps. stutzeri, Ps. cepacia* and *Ps. fluorescens* (WO 89/04361), or *Ps. plantarii* or *Ps. gladioli* (U.S. Pat. No. 4,950,417 (Solvay enzymes)) or *Ps. alcaligenes* and *Ps. pseudoalcaligenes* (EP 218 272) or *Ps. mendocina* (WO 88/09367; U.S. Pat. No. 5,389,536).

Fusarium, e.g. *F. oxysporum* (EP 130,064) or *F. solani pisi* (WO 90/09446).

Mucor (also called Rhizomucor), e.g. *M. miehei* (EP 238 023).

Chromobacterium (especially *C. viscosum*).

Aspergillus (especially *A. niger*).

Candida, e.g. *C. cylindracea* (also called *C. rugosa*) or *C. antarctica* (WO 88/02775) or *C. antarctica* lipase A or B (WO 94/01541 and WO 89/02916).

Geotricum, e.g. *G. candidum* (Schimada et al., (1989), J. Biochem., 106, 383–388).

Penicillium, e.g. *P. camembertii* (Yamaguchi et al., (1991), Gene 103, 61–67).

Rhizopus, e.g. *R. delemar* (Hass et al., (1991), Gene 109, 107–113) or *R. niveus* (Kugimiya et al., (1992) Biosci. Biotech. Biochem 56, 716–719) or *R. oryzae*.

Bacillus, e.g. *B. subtilis* (Dartois et al., (1993) Biochemica et Biophysica acta 1131, 253–260) or *B. stearothermophilus* (JP 64/7744992) or *B. pumilus* (WO 91/16422).

Specific examples of readily available commercial lipases include Lipolase®, Lipolase™ Ultra, Lipozyme®, Palatase®, Novozym® 435, Lecitase® (all available from Novo Nordisk A/S).

Examples of other lipases are Lumafast™, *Ps. mendocian* lipase from Genencor Int. Inc.; Lipomax™, *Ps. pseudoalcaligenes* lipase from Gist Brocades/Genencor Int. Inc.; *Fusarium solani* lipase (cutinase) from Unilever; Bacillus sp. lipase from Solvay enzymes. Other lipases are available from other companies.

It is to be understood that also lipase variants are contemplated as the parent enzyme. Examples of such are described in e.g. WO 93/01285 and WO 95/22615.

The activity of the lipase can be determined as described in "Methods of Enzymatic Analysis", Third Edition, 1984, Verlag Chemie, Weinhein, vol. 4, or as described in AF 95/5 GB (available on request from Novo Nordisk A/S).

Parent Oxidoreductases

Parent oxidoreductases (i.e. enzymes classified under the Enzyme Classification number E.C. 1 (Oxidoreductases) in accordance with the Recommendations (1992) of the International Union of Biochemistry and Molecular Biology (IUBMB)) include oxidoreductases within this group.

Examples include oxidoreductases selected from those classified under the Enzyme Classification (E.C.) numbers: Glycerol-3-phosphate dehydrogenase _NAD+_ (1.1.1.8), Glycerol-3-phosphate dehydrogenase _NAD (P)$^+$_ (1.1.1.94), Glycerol-3-phosphate 1-dehydrogenase _NADP_ (1.1.1.94), Glucose oxidase (1.1.3.4), Hexose oxidase (1.1.3.5), Catechol oxidase (1.1.3.14), Bilirubin oxidase (1.3.3.5), Alanine dehydrogenase (1.4.1.1), Glutamate dehydrogenase (1.4.1.2), Glutamate dehydrogenase _NAD(P)$^+$_ (1.4.1.3), Glutamate dehydrogenase _NADP$^+$_ (1.4.1.4), L-Amino acid dehydrogenase (1.4.1.5), Serine dehydrogenase (1.4.1.7), Valine dehydrogenase _NADP$^+$_ (1.4.1.8), Leucine dehydrogenase (1.4.1.9), Glycine dehydrogenase (1.4.1.10), L-Amino-acid oxidase (1.4.3.2.), D-Amino-acid oxidase(1.4.3.3), L-Glutamate oxidase (1.4.3.11), Protein-lysine 6-oxidase (1.4.3.13), L-lysine oxidase (1.4.3.14), L-Aspartate oxidase (1.4.3.16), D-amino-acid dehydrogenase (1.4.99.1), Protein disulfide reductase (1.6.4.4), Thioredoxin reductase (1.6.4.5), Protein disulfide reductase (glutathione) (1.8.4.2), Laccase (1.10.3.2), Catalase (1.11.1.6), Peroxidase (1.11.1.7), Lipoxygenase (1.13.11.12), Superoxide dismutase (1.15.1.1).

Said Glucose oxidases may be derived from *Aspergillus niger*.

Said Laccases may be derived from *Polyporus pinsitus, Myceliophtora thermophila, Coprinus cinereus, Rhizoctonia solani, Rhizoctonia praticola, Scytalidium thermophilum* and *Rhus verucaria*.

Bilirubin oxidases may be derived from *Myrothechecium verucaria*.

The Peroxidase may be derived from e.g. Soy bean, Horseradish or *Coprinus cinereus*.

The Protein Disulfide reductase may be any of the mentioned in DK patent applications No. 768/93, 265/94 and 264/94 (Novo Nordisk A/S), which are hereby incorporated as references, including Protein Disulfide reductases of bovine origin, Protein Disulfide reductases derived from *Aspergillus oryzae* or *Aspergillus niger*, and DsbA or DsbC derived from *Escherichia coli*.

Specific examples of readily available commercial oxidoreductases include Gluzyme™ (enzyme available from Novo Nordisk A/S). However, other oxidoreductases are available from others.

It is to be understood that also variants of oxidoreductases are contemplated as the parent enzyme.

The activity of oxidoreductases can be determined as described in "Methods of Enzymatic Analysis", third edition, 1984, Verlag Chemie, Weinheim, vol. 3.

Parent Carbohydrases

Parent carbohydrases may be defined as all enzymes capable of breaking down carbohydrate chains (e.g. starches) of especially five- and six-membered ring structures (i.e. enzymes classified under the Enzyme Classification number E.C. 3.2 (glycosidases) in accordance with the Recommendations (1992) of the International Union of Biochemistry and Molecular Biology (IUBMB)). Also included in the group of carbohydrases according to the invention are enzymes capable of isomerizing carbohydrates e.g. six-membered ring structures, such as D-glucose to e.g. five member ring structures like D-fructose.

Examples include carbohydrases selected from those classified under the Enzyme Classification (E.C.) numbers:

α-amylase (3.2.1.1) β-amylase (3.2.1.2), glucan 1,4-α-glucosidase (3.2.1.3), cellulase (3.2.1.4), endo-1,3(4)-β-glucanase (3.2.1.6), endo-1,4-β-xylanase (3.2.1.8), dextranase (3.2.1.11), chitinase (3.2.1.14), polygalacturonase (3.2.1.15), lysozyme (3.2.1.17), β-glucosidase (3.2.1.21), α-galactosidase (3.2.1.22), β-galactosidase (3.2.1.23), amylo-1,6-glucosidase (3.2.1.33), xylan 1,4-β-xylosidase (3.2.1.37), glucan endo-1,3-β-D-glucosidase (3.2.1.39), α-dextrin endo-1,6-glucosidase (3.2.1.41), sucrose α-glucosidase (3.2.1.48), glucan endo-1,3-α-glucosidase (3.2.1.59), glucan 1,4-β-glucosidase (3.2.1.74), glucan endo-1,6-β-glucosidase (3.2.1.75), arabinan endo-1,5-α-arabinosidase (3.2.1.99), lactase (3.2.1.108), chitonanase (3.2.1.132) and xylose isomerase (5.3.1.5).

Examples of relevant carbohydrases include α-1,3-glucanases derived from *Trichoderma harzianum;* α-1,6-glucanases derived from a strain of Paecilomyces; β-glucanases derived from *Bacillus subtilis;* β-glucanases derived from *Humicola insolens;* β-glucanases derived from *Aspergillus niger;* β-glucanases derived from a strain of Trichoderma; β-glucanases derived from a strain of *Oerskovia xanthineolytica;* exo-1,4 -α-D-glucosidases (glucoamylases) derived from *Aspergillus niger;* α-amylases derived from *Bacillus subtilis;* α-amylases derived from *Bacillus amyloliquefaciens;* α-amylases derived from *Bacillus stearothermophilus;* α-amylases derived from *Aspergillus oryzae;* α-amylases derived from non-pathogenic microorganisms; α-galactosidases derived from *Aspergillus niger;* Pentosanases, xylanases, cellobiases, cellulases, hemi-cellulases deriver from *Humicola insolens;* cellulases derived from *Trichoderma reesei;* cellulases derived from non-pathogenic mold; pectinases, cellulases, arabinases, hemi-celluloses derived from *Aspergillus niger;* dextranases derived from *Penicillium lilacinum;* endo-glucanase derived from non-pathogenic mold; pullulanases derived from *Bacillus acidopullyticus;* β-galactosidases derived from *Kluyveromyces fragilis;* xylanases derived from *Trichoderma reesei.*

Specific examples of readily available commercial carbohydrases include Alpha-Gal™, Bio-Feed™ Alpha, Bio-Feed™ Beta, Bio-Feed™ Plus, Bio-Feed™ Plus, Novozyme® 188, Carezyme®, Celluclast®, Cellusoft®, Ceremyl®, Citrozym™, Denimax™, Dezyme™, Dextrozyme™, Finizym®, Fungamyl™, Gamanase™, Glucanex®, Lactozym®, Maltogenase™, Pentopan™, Pectinex™, Promozyme®, Pulpzyme™, Novamyl™, Termamyl®, AMG (Amyloglucosidase Novo), Maltogenase®, Sweetzyme®, Aquazym®, Natalase® (all enzymes available from Novo Nordisk A/S). Other carbohydrases are available from other companies.

It is to be understood that also carbohydrase variants are contemplated as the parent enzyme.

The activity of carbohydrases can be determined as described in "Methods of Enzymatic Analysis", third edition, 1984, Verlag Chemie, Weinheim, vol. 4.

Parent Transferases

Parent transferases (i.e. enzymes classified under the Enzyme Classification number E.C. 2 in accordance with the Recommendations (1992) of the International Union of Biochemistry and Molecular Biology (IUBMB)) include transferases within this group.

The parent transferases may be any transferase in the subgroups of transferases: transferases transferring one-carbon groups (E.C. 2.1); transferases transferring aldehyde or residues (E.C 2.2); acyltransferases (E.C. 2.3); glucosyl-transferases (E.C. 2.4); transferases transferring alkyl or aryl groups, other that methyl groups (E.C. 2.5); transferases transferring nitrogeneous groups (2.6).

In a preferred embodiment the parent transferase is a transglutaminase E.C 2.3.2.13 (Protein-glutamine μ-glutamyltransferase).

Transglutaminases are enzymes capable of catalyzing an acyl transfer reaction in which a gamma-carboxyamide group of a peptide-bound glutamine residue is the acyl donor. Primary amino groups in a variety of compounds may function as acyl acceptors with the subsequent formation of monosubstituted gamma-amides of peptide-bound glutamic acid. When the epsilon-amino group of a lysine residue in a peptide-chain serves as the acyl acceptor, the transferases form intramolecular or intermolecular gamma-glutamyl-epsilon-lysyl crosslinks.

Examples of transglutaminases are described in the pending DK patent application no. 990/94 (Novo Nordisk A/S).

The parent transglutaminase may be of human, animal (e.g. bovine) or microbial origin.

Examples of such parent transglutaminases are animal derived Transglutaminase, FXIIIa; microbial transglutaminases derived from *Physarum polycephalum* (Klein et al., Journal of Bacteriology, Vol. 174, p. 2599–2605); transglutaminases derived from Streptomyces sp., including *Streptomyces lavendulae, Streptomyces lydicus* (former *Streptomyces libani*) and Streptoverticillium sp., including *Streptoverticillium mobaraense, Streptoverticillium cinnamoneum,* and *Streptoverticillium griseocarneum* (Motoki et al., U.S. Pat. No. 5,156,956; Andou et al., U.S. Pat. No. 5,252,469; Kaempfer et al., Journal of General Microbiology, Vol. 137, p. 1831–1892; Ochi et al., International Journal of Sytematic Bacteriology, Vol. 44, p. 285–292; Andou et al., U.S. Pat. No. 5,252,469; Williams et al., Journal of General Microbiology, Vol. 129, p. 1743–1813).

It is to be understood that also transferase variants are contemplated as the parent enzyme.

The activity of transglutaminases can be determined as described in "Methods of Enzymatic Analysis", third edition, 1984, Verlag Chemie, Weinheim, vol. 1–10.

Parent Phytases

Parent phytases are included in the group of enzymes classified under the Enzyme Classification number E.C. 3.1.3 (Phosphoric Monoester Hydrolases) in accordance with the Recommendations (1992) of the International Union of Biochemistry and Molecular Biology (IUBMB)).

Phytases are enzymes produced by microorganisms which catalyze the conversion of phytate to inositol and inorganic phosphorus.

Phytase producing microorganisms comprise bacteria such as *Bacillus subtilis, Bacillus natto* and Pseudomonas; yeasts such as *Saccharomyces cerevisiae;* and fungi such as *Aspergillus niger, Aspergillus ficuum, Aspergillus awamori, Aspergillus oryzae, Aspergillus terreus* or *Aspergillus nidulans,* and various other Aspergillus species).

Examples of parent phytases include phytases selected from those classified under the Enzyme Classification (E.C.) numbers: 3-phytase (3.1.3.8) and 6-phytase (3.1.3.26).

The activity of phytases can be determined as described in "Methods of Enzymatic Analysis", third edition, 1984, Verlag Chemie, Weinheim, vol. 1–10, or may be measured according to the method described in EP-A1-0 420 358, Example 2 A.

Lyases

Suitable lyases include Polysaccharide lyases: Pectate lyases (4.2.2.2) and pectin lyases (4.2.2.10), such as those from *Bacillus licheniformis* disclosed in WO 99/27083.

Another aspect of the invention is a composition comprising at least one protein (polypeptide) or enzyme of the invention. The composition may comprise other polypeptides, proteins or enzymes and/or ingredients normally used in personal care products, such as shampoo, soap bars, skin lotion, skin creme, hair dye, toothpaste, household articles, agro chemicals, personal care products, such as cleaning preparations e.g. for contact lenses, cosmetics, toiletries, oral and dermal pharmaceuticals, compositions used for treating textiles, compositions used for manufacturing food, e.g. baking, and feed etc.

Examples of said proteins(polypeptides)/enzymes include enzymes exhibiting protease, lipase, oxidoreductase, carbohydrase, transferase, such as transglutaminase, phytase and/or anti-microbial polypeptide activity. These enzymes may be present as conjugates with reduced activity.

The protein of the invention may furthermore typically be used in a detergent composition. It may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238 216.

The detergent composition may be in any convenient form, e.g. as powder, granules, paste or liquid. A liquid detergent may be aqueous, typically containing up to 70% water and 0–30% organic solvent, or non-aqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or is more other enzymes, such as e.g. proteases, amylases, lipases, cutinases, cellulases, peroxidases, oxidases, and further anti-microbial polypeptides.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfon-ate (NOBS). Alternatively, the bleaching system may comprise peroxyacids of, e.g., the amide, imide, or sulfone type.

The detergent composition of the invention comprising the polypeptide of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition, agents, dyes, bactericides, optical brighteners, or perfume.

The pH (measured in aqueous solution at use concentration) will usually be neutral or alkaline, e.g. in the range of 7–11.

Dishwashing Composition

Further, a modified enzyme according to the invention may also be used in dishwashing detergents.

Dishwashing detergent compositions comprise a surfactant which may be anionic, non-ionic, cationic, amphoteric or a mixture of these types. The detergent will contain 0–90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders, when present, include the water-soluble salts especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymetoxy succinates, ammonium polyacetates, carboxylates, polycarbbxylates, aminopolycarboxylates, polyacetyl carboxylates and polyhydroxsulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as e.g. propylene glycol, a sugar or a sugar alcohol, lactic acid, boric acid, or a boric acid derivative, e.g. an aromatic borate ester.

The dishwashing detergent composition of the invention may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the enzyme of the invention may be used in conventional dishwashing-detergents, e.g. in any of the detergents described in any of the following patent publications: EP 518719, EP 518720, EP 518721, EP 516553, EP 516554, EP 516555, GB 2200132, DE 3741617, DE 3727911, DE 4212166, DE 4137470, DE 3833047, WO 93/17089, DE 4205071, WO 52/09680, WO 93/18129, WO 93/04153, WO 92/06157, WO 92/08777, EP 429124, WO 93/21299, U.S. Pat. No. 5,141,664, EP 561452, EP 561446, GB 2234980, WO 93/03129, EP 481547, EP 530870, EP 533239, EP 554943, EP 346137, U.S. Pat. No. 5,112,518, EP 318204, EP 318279, EP 271155, EP 271156, EP 346136, GB 2228945, CA 2006687, WO 93/25651, EP 530635, EP 414197, U.S. Pat. No. 5,240,632.

Personal Care Applications

The protein of the invention is also of interest in connection with personal care applications.

Proteases

Proteases are well-known active ingredients for cleaning of contact lenses. They hydrolyze the proteinaceous soil on the lens and thereby make it soluble. Removal of the protein soil is essential for the wearing comfort.

Proteases are also effective ingredients in skin cleaning products, where they remove the upper layer of dead keratinaseous skin cells and thereby make the skin look brighter and fresher.

Proteases are also used in oral care products, especially for cleaning of dentures, but also in dentifrices.

Further, proteases are used in toiletries, bath and shower products, including shampoos, conditioners, lotions, creams, soap bars, toilet soaps, and liquid soaps.

Lipases

Lipases can be applied for cosmetic use as active ingredients in skin cleaning products and anti-acne products for removal of excessive skin lipids, and in bath and shower products such as creams and lotions as active ingredients for skin care.

Lipases can also be used in hair cleaning products (e.g. shampoos) for effective removal of sebum and other fatty material from the surface of hair.

Lipases are also effective ingredients in products for cleaning of contact lenses, where they remove lipid deposits from the lens surface.

Oxidoreductases

The most common oxidoreductase for personal care purposes is an oxidase (usually glucose oxidase) with substrate (e.g. glucose) that ensures production of $H_2O_2$, which then will initiate the oxidation of for instance $SCN^-$ or $I^-$ into antimicrobial reagents ($SCNO^-$ or $I_2$) by a peroxidase (usually lactoperoxidase). This enzymatic complex is known in nature from e.g. milk and saliva.

It is being utilized commercially as an anti-microbial system in oral care products (mouth rinse, dentifrice, chewing gum) where it also can be combined with an amyloglucosidase to produce the glucose. These systems are also known in cosmetic products for preservation.

Anti-microbial systems comprising the combination of an oxidase and a peroxidase are known in the cleaning of contact lenses.

Another application of oxidoreductases is oxidative hair dyeing using oxidases, peroxidases and laccases.

Free radicals formed on the surface of the skin (and hair) known to be associated with the ageing process of the skin (spoilage of the hair). The free radicals activate chain reactions that lead to destruction of fatty membranes, collagen, and cells. The application of free radical scavengers such as Superoxide dismutase into cosmetics is well known (R. L. Goldemberg, DCI, November 93, p. 48–52).

Protein disulfide isomerase (PDI) is also an oxidoreductase. It can be utilized for waving of hair (reduction and reoxidation of disulfide bonds in hair) and repair of spoiled hair (where the damage is mainly reduction of existing disulfide bonds).

Carbohydrases

Plaque formed on the surface of teeth is composed mainly of polysaccharides. They stick to the surface of the teeth and the microorganisms. The polysaccharides are mainly $\alpha$-1,6 bound glucose (dextran) and $\alpha$-1,3 bound glucose (mutan). The application of different types of glucanases such as mutanase and dextranase helps hydrolyzing the sticky matrix of plaque, making it easier to remove by mechanical action.

Also other kinds of biofilm for instance the biofilm formed in lens cases can be removed by the action of glucanases.

Food and Feed

Further conjugated enzymes or polypeptides with reduced immunogenicity according to the invention may advantageously be used in the manufacturing of food and feed.

Proteases

The gluten in wheat flour is the essential ingredient responsible for the ability of flour to be used in baked foodstuffs. Proteolytic enzymes are sometimes needed to modify the gluten phase of the dough, e.g. a hard wheat flour can be softened with a protease.

Neutrase® is a commercially available neutral metallo protease that can be used to ensure a uniform dough quality and bread texture, and to improve flavor. The gluten proteins are degraded either moderately or more extensively to peptides, whereby close control is necessary in order to avoid excessive softening of the dough.

Proteases are also used for modifying milk protein.

To coagulate casein in milk when producing cheese proteases such as rennet or chymosin may be used.

In the brewery industry proteases are used for brewing with unmalted cereals and for controlling the nitrogen content.

In animal feed products proteases are used so to speak to expand the animals' digestion system.

Lipases

The application of lipase in the baking industry is rather new. Addition of lipase results in improved dough properties and an improved breadmaking quality in terms of larger volume, improved crumb structure and whiter crumb color. The observed effect can be explained by a mechanism where the lipase changes the interaction between gluten and some lipids fragment during dough mixing. This results in an improved gluten network.

The flavor development of blue roan cheese (e.g. Danablue), certain Italian type cheese, and other dairy products containing butter-fat, are dependent on the degradation of milk fat into free fatty acids. Lipases may be used for developing flavor in such products.

In the oil- and fat-producing industry lipases are used e.g. to minimize the amount of undesirable side-products, to modify fats by interesterification, and to synthesis of esters.

Oxidoreductases

Further oxidoreductases with reduced immunogenicity according to the invention may advantageously be used in the manufacturing of food and feed.

Several oxidoreductases are used for baking, glucose oxidase, lipoxygenase, peroxidase, catalase and combinations hereof. Traditionally, bakers strengthen gluten by adding ascorbic acid and potassium bromate. Some oxidoreductases can be used to replace bromate in dough systems by oxidation of free sulfydryl units in gluten proteins. Hereby disulphide linkages are formed resulting in stronger, more elastic doughs with greater resistance.

Gluzyme™ (Novo Nordisk A/S) is a glucose oxidase preparation with catalase activity that can be used to replace bromate. The dough strength is measured as greater resistance to mechanical shock, better oven spring and larger loaf volume.

Carbohydrases

Flour has varying content of amylases leading to differences in the baking quality. Addition of amylases can be necessary in order to standardize the flour. Amylases and pentosanases generally provide sugar for the yeast fermentation, improve the bread volume, retard retrogradation, and decrease the staling rate and stickiness that results from pentosan gums. Examples of carbohydrases are given below.

Certain maltogenic amylases can be used for prolonging the shelf life of bread for two or more days without causing gumminess in the product. Selectively modifies the gelatinized starch by cleaving from the non-reducing end of the starch molecules, low molecular weight sugars and dextrins. The starch is modified in such a way that retrogradation is less likely to occur. The produced low-molecular-weight sugars improve the baked goods' water retention capacity without creating the intermediate-length dextrins that result in gumminess in the finished product. The enzyme is inactivated during bread baking, so it can be considered a processing aid that does not have to be declared on the label. Overdosing of Novamyl can almost be excluded.

The bread volume can be improved by fungal α-amylases which further provide good and uniform structure of the bread crumb. Said α-amylases are endoenzymes that produce maltose, dextrins and glucose. Cereal and some bacterial α-amylases are inactivated at temperatures above the gelatinization temperature of starch, therefore when added to wheat dough it results in a low bread volume and a sticky bread interior. Fungamyl has the advantage of being thermolabile and is inactivated just below the gelatinization temperature.

Enzyme preparations containing a number of pentosanase and hemi-cellulase activities can improve the handling and stability of the dough, and improves the freshness, the crumb structure and the volume of the bread.

By hydrolyzing the pentosans fraction in flour, it will lose a great deal of its water-binding capacity, and the water will then be available for starch and gluten. The gluten becomes more pliable and extensible, and the starch gelatinizes more easily. Pentosanases can be used in combination with or as an alternative to emulsifiers.

Further, carbohydrases are used for producing syrups from starch, which are widely used in soft drinks, sweets, meat products, dairy products, bread products, ice cream, baby food, jam etc.

The conversion of starch is normally carried out in three steps. First the starch is liquefied by the use of α-amylases. Maltodextrins, primarily consisting of oligosaccharides and dextrins, are obtained.

The mixture is then treated with an amyloglucosidase for hydrolyzing the oligosaccharides and dextrins into glucose. This way a sweeter product is obtained. If high maltose syrups are desired β-amylases alone or in combination with a pullulanase (de-branching enzyme) may be used.

The glucose mixture can be made even sweeter by isomerization to fructose. For this an immobilized glucose isomerase can be used.

In the sugar industry, it is common practice to speed up the breakdown of present starch in cane juices. The starch content in the raw sugar is thereby reduced and filtration at the refinery facilitated.

Furthermore, dextranases are used to break down dextran in raw sugar juices and syrups.

In the alcohol industry α-amylases are advantageously being used for thinning of starch in distilling mashes.

In the brewing industry α-amylases are used for adjunct liquefaction.

In the dairy industry β-galactosidases (lactase) are used when producing low lactose milk for persons suffering from lactose malabsorption.

When flavored milk drinks are produced from lactase-treated milk, the addition of sugar can be reduced without reducing the sweetness of the product.

In the production of condensed milk, lactose crystallization can be avoided by lactase treatment, and the risk of thickening caused by casein coagulation in lactose crystals is thus reduced.

When producing ice cream made from lactase-treated milk (or whey) no lactose crystals will be formed and the defect, sandiness, will not occur.

Further, xylanases are known to be used within a number of food/feed industrial applications as described in WO 94/21785 (Novo Nordisk A/S).

α-amylases are used in the animal feed industry to be added to cereal-containing feed to improve the digestibility of starch.

Anti-microbial Polypeptides

Certain bacteriolytic enzymes may be used e.g. to wash carcasses in the meat packing industry (see U.S. Pat. No. 5,354,681 from Novo Industri A/S).

Transferases

Transglutaminases with reduced immunogenicity according to the invention may advantageously be used in the manufacturing of food and feed.

Transglutaminases have the ability for crosslinking protein.

This property can be used for gelling of aqueous phases containing proteins. This may be used when producing spreads (DK patent application no. 1071/84 from Novo Nordisk A/S).

Transglutaminases are being used for improvement of baking quality of flour e.g. by modifying wheat flour to be used in the preparation of cakes with improved properties, such as improved taste, dent, mouth-feel and a higher volume (see JP 1-110147).

Further producing paste type food material e.g. used as fat substitution in foods sucg as ice cream, toppings, frozen desserts, mayonnaises and low fat spreads (see WO 93/22930 from Novo Nordisk A/S).

Furthermore, for preparation of gels for yogurt, mousses, cheese, puddings, orange juice, from milk and milk-like products, and binding of chopped meat product, improvement of taste and texture of food proteins (see WO 94/21120 and WO 94/21129 from Novo Nordisk A/S).

Phytases

Phytases of the invention may advantageously be used in the manufacturing of food, such as breakfast cereal, cake, sweets, drinks, bread or soup etc., and animal feed.

Phytases may be used either for exploiting the phosphorus bound in the phytate/phytic acid present in vegetable protein sources or for exploiting the nutritionally important minerals bound in phytic acid complexes.

Microbial phytase may be added to feedstuff of monogastric animals in order to avoid supplementing the feed with inorganic phosphorus (see U.S. Pat. No. 3,297,548).

Further, phytases may be used in soy processing. Soyabean meal may contain high levels of the anti-nutritional factor phytate which renders this protein source unsuitable for application in baby food and feed for fish, calves and other non-ruminants, since the phytate chelates essential minerals present therein (see EP 0 420 358).

Also for baking purposes phytases may be used. Bread with better quality can be prepared by baking divided pieces of a dough containing wheat flour etc. and phytase (see JP-0-3076529-A).

A high phytase activity as in koji mold is known to be used for producing refined sake (see JP-0-6070749-A).

Textile Applications

Proteases

Proteases are used for degumming and sand washing of silk.

Lipases

Lipases are used for removing fatty matter containing hydrophobic esters (e.g. triglycerides) during the finishing of textiles (see e.g. WO 93/13256 from Novo Nordisk A/S).

Oxidoreductases

In bleach clean up of textiles catalases may serve to remove excess hydrogen peroxide.

Carbohydrases

Cellulolytic enzymes are widely used in the finishing of denim garments in order to provide a localized variation in the color density of the fabric (Enzyme facilitated "stone wash").

Also cellulolytic enzymes find use in the bio-polishing process. Bio-Polishing is a specific treatment of the yarn surface which improves fabric quality with respect to handle and appearance without loss of fabric wettability. Bio-polishing may be obtained by applying the method described e.g. in WO 93/20278.

During the weaving of textiles, the threads are exposed to considerable mechanical strain. In order to prevent breaking, the threads are usually reinforced by the coating (sizing) with a gelatinous substance (size). The most common sizing agent is starch in native or modified form. A uniform and durable finish can thus be obtained only after removal of the size from the fabric, the so-called desizing. Desizing of fabrics sized with a size containing starch or modified starch is preferably facilitated by use of amylolytic enzymes.

Oral and Dermal Pharmaceuticals

Proteases

Different combinations of highly purified proteases (e.g. Trypsin and Chymotrypsin) are used in pharmaceuticals to be taken orally, and dermal pharmaceuticals for combating e.g. inflammations, edemata and injuries.

Leather Production

Transferase

Transglutaminase is known to be used to casein-finishing leather by acting as a hardening agent (see WO 94/13839 from Novo Nordisk).

Hard Surface Cleaning

Cleaning of hard surfaces e.g. in the food industry is often difficult, as equipment used for producing dairies, meat, sea food products, beverages etc. often have a complicated shape. The use of surfactant compositions in the form of gels and foams comprising enzymes have been shown to facilitate and improve hard surface cleaning. Enzymes, which advantageously may be added in such surfactant compositions, are in particular proteases, lipases, amylases and cellulases.

Such hard surface cleaning compositions comprising enzymes may also advantageously be used in the transport sector, for instance for washing cars and for general vessel wash.

Finally the invention relates to the use of the protein of the invention or a composition of the invention in products comprising polypeptides.

First of all the conjugate or compositions of the invention can advantageously be used for personal care products, such as hair care and hair treatment products. This include products such as shampoo, balsam, hair conditioners, hair waving compositions, hair dyeing compositions, hair tonic, hair liquid, hair cream, shampoo, hair rinse, hair spray.

Further contemplated are oral care products such as dentifrice, oral washes, chewing gum.

Also contemplated are skin care products and cosmetics, such as skin cream, skin milk, cleansing cream, cleansing lotion, cleansing milk, cold cream, cream soap, nourishing essence, skin lotion, milky lotion, calamine lotion, hand cream, powder soap, transparent soap, sun oil, sun screen, shaving foam, shaving cream, baby oil lipstick, lip cream, creamy foundation, face powder, powder eye-shadow, powder, foundation, make-up base, essence powder, whitening powder.

Also for contact lenses hygiene products the conjugate of the invention can be used advantageously. Such products include cleaning and disinfection products for contact lenses.

The use of detergents such as washing powder, soap, soap bars and liquid soap are also contemplated.

Furthermore, this invention relates to the method by which the protein variants are being synthesized and expressed in host cells. This is achieved by culturing host cells capable of expressing a polypeptide in a suitable culture medium to obtain expression and secretion of the polypeptide into the medium, followed by isolation of the polypeptide from the culture medium. The host cell may be any cell suitable for the large-scale production of proteins, capable of expressing a protein and being transformed by an expression vector.

The host cell comprises a DNA construct as defined above, optionally the cells may be transformed with an expression vector comprising a DNA construct as defined above. The host cell is selected from any suitable cell, such as a bacterial cell, a fungal cell, an animal cell, such as an insect cell or a mammalian cell, or a plant cell.

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, Molecular General Genetics 168:111–115), by using competent cells (see, e.g., Young and Spizizin, 1961, Journal of Bacteriology 81:823–829, or Dubnar and Davidoff-Abelson, 1971, Journal of Molecular Biology 56:209–221), by electroporation (see, e.g., Shigekawa and Dower, 1988, Biotechniques 6:742–751), or by conjugation (see, e.g., Koehler and Thorne, 1987, Journal of Bacteriology 169:5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota includemushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of zygomycota include, e.g., Rhizopus and Mucor.

In a preferred embodiment, the fungal host cell is a yeast cell. "Yeast" as used herein includes ascosporogenous yeast (Endomycetales), basidiosporogenous yeast, and yeast belonging to the *Fungi Imperfecti* (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the *Fungi Imperfecti* are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast Saccharomyces, Strathern et al., editors, 1981).

In a more preferred embodiment, the yeast host cell is a cell of the species of Candida, Kluyveromyces, Saccharomyces, Schizosaccharomyces, Pichia, or Yarrowia.

In another preferred embodiment, the yeast host cell is a *Saccharomyces uvae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica,* Candida sp., *Candida utilis, Candida cacaoi,* Geotrichum sp., *Geotrichum fermentans,* preferably *Saccharomyces cerevisiae.*

In another embodiment, protein variants may be produced in cells selected among other fungi, such as Aspergillus spp, or *Humicola lanuginosa* or *Aspergillus oryzae.*

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma or a teleomorph or synonym thereof.

Further in a preferred embodiment, the filamentous fungal host cell is an Aspergillus cell.

In yet another preferred embodiment, the filamentous fungal host cell is an Acremonium cell, a Fusarium cell, a Humicola cell, a Mucor cell, a Myceliophthora cell, a Neurospora cell, a Penicillium cell, a Thielavia cell, a Tolypocladium cell or a Trichoderma cell.

In a more preferred embodiment, the filamentous fungal host cell is an *Aspergillus awamori, Aspergillus foetidus, Aspergillus japonicus, Aspergillus niger* or *Aspergillus oryzae* cell.

In another preferred embodiment, the filamentous fungal host cell is a Fusarium cell of the section Discolor (also known as the section Fusarium). For example, the filamentous fungal parent cell may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum,* or *Fusarium trichothecioldes* cell.

In yet another preferred embodiment, the filamentous fungal parent cell is a Fusarium strain of the section Elegans, e.g., *Fusarium oxysporum*.

Furthermore in another preferred embodiment, the filamentous fungal host cell is a *Humicola insolens,* a *Humicola lanuginosa* cell, a *Mucor miehei* cell, a *Myceliophthora thermophilum* cell, a *Neurospora crassa* cell, a *Penicillium purpurogenum* cell, a *Thielavia terrestris* cell.

In another preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81:1470–1474. A suitable method of transforming Fusarium species is described by Malardier et al., 1989, Gene 78:147–156 or in copending U.S. Ser. No. 08/269,449. Yeast may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153:163; and Hinnen et al., 1978, Proceedings of the National Academy of Sciences USA 75:1920. Mammalian cells may be transformed by direct uptake using the calcium phosphate precipitation method of Graham and Van der Eb (1978, Virology 52:546).

In yet another embodiment the host is selected among plant cells, such as potato cells, or the host is selected among animal cells, such as insect cells, for example *Spodoptera frugiperda* Sf9 and Sf21 ovary cells and High Five Line from *Trichoplusia ni* eggs, or mammalian cells, such as monkey CV1 and COS cells, murine C127 fibroblasts and chines hamster ovary cells (CHO).

The expression vector may be any vector to be subjected to the procedure of recombinant DNA, followed by successful expression in a host organism. When introduced into the cell the vector may function in an autonome fashion. With a replication origin a plasmid can replicate independently of the host cell. Alternatively it can be incorporated into the host cell genome, and be replicated together with the host cell genome.

Another embodiment of the invention relates to the use of a random peptide display package library, such as a phage display system for selecting a protein variant as described above.

EXAMPLES

Example 1

Epitope Patterns

Screening a random phage display peptide library with IgG antibodies raised against the parent protein revealed the following epitope patterns.

Sequences marked with(*) may exist in the context of a Cys-Cys bridge.

Bold: anchor amino acid

Italic: conservative mutations

TABLE 1

| | | |
|---|---|---|
| 1) | | Parent protein laccase |
| | | Epitope patterns |
| | 1. | P R *S* D P G T P *T* (SEQ ID NO: 1) |
| | | P R *T* D P G W L *A* (SEQ ID NO: 2) |
| | | P S *S* D P G A R *S* (SEQ ID NO: 3) |
| | 2. | W P K S D A G D S (SEQ ID NO: 4) |
| | | G P S R D A G L L (SEQ ID NO: 5) |
| | 3. | G P S R D A G L *L* (SEQ ID NO: 6) |
| | | G A A R D A R S *A* (SEQ ID NO: 7) |
| | 4. | H V F D K N V T R (SEQ ID NO: 8) |
| 2) | | Parent protein JE-1 (NATALASE) (amylase): |
| | | Epitope patterns |
| | 1. | Q L Y G D E Q L P (SEQ ID NO: 9) |
| | 2. | G S A T I D P R Q (*) (SEQ ID NO: 10) |
| 3) | | Parent protein Lipoprime: |
| | | Epitope patterns |
| | 1. | H E *Y* P M D F H L (SEQ ID NO: 11) |
| | | S E Y S M S I T P (SEQ ID NO: 12) |
| | | P E Y T M N A L S (SEQ ID NO: 13) |
| | 2. | Q R P P R Y E L E (SEQ ID NO: 14) |
| | 3. | R K L T L S G R S (SEQ ID NO: 15) |
| 4) | | Parent protein PD498 (protease): |
| | | Epitope patterns |
| | 1. | T *R* Y H *R R* P P L (SEQ ID NO: 16) |
| | | S R Y N *K K* P H L (SEQ ID NO: 17) |
| | 2. | N K L A T R E P M (SEQ ID NO: 18) |
| | 3. | V N H F R K R S A (SEQ ID NO: 19) |
| | 4. | R G L S M I M G K (SEQ ID NO: 20) |
| 5) | | Parent protein Carezyme(*) |
| | | Epitope patterns |
| | 1. | V H A G P R A G T (SEQ ID NO: 21) |
| | | V H S G P R A G Y (SEQ ID NO: 22) |
| | | V H A G P R A G T (SEQ ID NO: 23) |
| | 2. | V H A G P R A G *T* (SEQ ID NO: 24) |
| | | V H A G P R A G *T* (SEQ ID NO: 25) |
| | | V T R G P N A G *S* (SEQ ID NO: 26) |
| | 3. | V H A G P R A G T (SEQ ID NO: 27) |
| | | V H S G P R A G Y (SEQ ID NO: 28) |
| | | V H A G P R A G T (SEQ ID NO: 29) |
| | | V H A G P R A G T (SEQ ID NO: 30) |
| | | V H A G P R A G T (SEQ ID NO: 31) |
| | | V T R G P N A G S (SEQ ID NO: 32) |
| | | L S G P L A G R V (SEQ ID NO: 33) |
| 6) | | Parent protein Savinase: |
| | | Epitope patterns |
| | 1. | F N D A F F V K M (SEQ ID NO: 34) |
| | | T F H D A P A L Q (SEQ ID NO: 35) |
| | 2. | T F H D A P A *L* Q (SEQ ID NO: 36) |
| | | D F H V K Y A A Q (SEQ ID NO: 37) |
| | 3. | A N P I W S R S A (SEQ ID NO: 38) |
| | 4. | T A R L R A G N A (*) (SEQ ID NO: 39) |
| | 5. | R A F R R N A N W (SEQ ID NO: 40) |

Example 2

Epitope Mapping Using Phage Display Libraries and 3D Analysis

Identification of Epitope Sequences and Epitope Patterns

High diversity libraries ($10^{12}$) of phages expressing random hexa-, nona- or dodecapetides as part of their membrane proteins, were screened for their capacity to bind purified specific rabbit IgG, and purified rat and mouse IgG1 and IgE antibodies. The phage libraries were obtained according to prior art (se WO 92/15679 hereby incorporated by reference).

The antibodies were raised in the respective animals by subcutanuous, intradermal or intratracheal injection of relevant proteins (f.e. proteases, lipases, amylases, oxidoreductases) dissolved in phosphate buffered saline (PBS). The respective antibodies were purified from the serum of immunised animals by affinity chromatography using paramagnetic immunobeads (Dynal AS) loaded with pig anti-rabbit IgG, mouse anti-rat IgG1 or IgE, or rat anti-mouse IgG1 or IgE antibodies.

The respective phage libraries were incubated with the IgG, IgG1 and IgE antibody coated beads. Phages expressing oligopeptides with affinity for rabbit IgG, or rat or mouse IgG1 or IgE antibodies, were collected by exposing these paramagnetic beads to a magnetic field. The collected phages were eluted from the immobilised antibodies by mild acid treatment, or by elution with intact enzyme. The isolated phages were amplified as know to the specialist. Alternatively, immobolised phages were directly incubated with *E. coli* for infection. In short, F-factor positive *E. coli* (f.e XL-1 Blue, JM101, TG1) were infected with M13-derived vector in the presence of a helper-phage (f.e. M13K07), and incubated, typically in 2×YT containing glucose or IPTG, and appropriate antibiotics for selection. Finally, cells were removed by centrifugation. This cycle of events was repeated on the respective cell supernatants, minimal 2× and maximal 5×. After selection round 2, 3, 4 and 5, a fraction of the infected *E. coli* was incubated on selective 2×YT agar plates, and the specificity of the emerging phages was assessed immunologically. Thus, phages were transferred to a nitrocellulase (NC) membrane. For each plate, 2 NC-replicas were made. One replica was incubated with the selection antibodies, the other replica was incubated with the selection antibodies and the immunogen used to obtain the antibodies as competitor. Those plaques that were absent in the presence of immunogen, were considered specific, and were amplified according to the procedure described above.

The specific phage-clones were isolated from the cell supernatant by centrifugation in the presence of polyethylenglycol. DNA was isolated, the DNA sequence coding for the oligopeptide was amplified by PCR, and the DNA sequence was determined, all according to standard procedures. The amino acid sequence of the corresponding oligopeptide was deduced from the DNA sequence.

Thus, a number of peptide sequences with specificity for the protein specific antibodies, described above, were obtained. These sequences were collected in a database, and analysed by sequence alignment to identify epitope patterns. Conservative exhanges (e.g. aspartate for glutamate, lysine for arginine, serine for threonine) were considered as one. This showed that most sequences were specific for the protein the antibodies were raised against. However, several cross-reacting sequences were obtained from phages that went through 2 selection rounds only. Yet, 22 epitope paterns were identified.

The epitope paterns are shown in table 2 below.

TABLE 2

An extract from the epitope-database.

| Sequence alignment | Enzyme | Epitope pattern |
| --- | --- | --- |
| T R Y H > R R P P L (SEQ ID NO: 41) | PD498 | RYPR (SEQ ID NO: 88) |
| S R Y N > K K P H L (SEQ ID NO: 42) | PD498 | K |
| R R Y P > K L M P P (SEQ ID NO: 43) | PD498 | |
| R R Y S > Q R T I Q (SEQ ID NO: 44) | PD498 | |
| C V H S G P R A G Y C G (SEQ ID NO: 45) | Carezyme | SGPRAG (SEQ ID NO: 89) |
| C I T S G P R A G N C G (SEQ ID NO: 46) | Carezyme | T |
| C > L S G P L A G R V C G (SEQ ID NO: 47) | Carezyme | |
| P R S D P G T P T (SEQ ID NO: 48) | Laccase | PRSDPG (SEQ ID NO: 90) |
| P R T D P G W L A (SEQ ID NO: 49) | Laccase | K |
| P S S D P G A R S (SEQ ID NO: 50) | Laccase | |
| P > R S D T G F G (SEQ ID NO: 51) | Laccase | DP > RDTG (SEQ ID NO: 91) |
| D P V R D > T G A G (SEQ ID NO: 52) | Laccase | |
| D P A R D > T G D V (SEQ ID NO: 53) | Laccase | |
| R A F R R N A > N W (SEQ ID NO: 54) | Savinase | AR > R > A > N (SEQ ID NO: 92) |
| C T A R L R > A G N A C G (SEQ ID NO: 55) | Savinase | |
| C T A R V V > A L G V C G (SEQ ID NO: 56) | Savinase | |
| F C T N N C E L S (SEQ ID NO: 57) | Savinase | NN > EL (SEQ ID NO: 93) |
| R R F S N N D E L (SEQ ID NO: 58) | Savinase | |
| K R F A N > T E L A (SEQ ID NO: 59) | Savinase | |
| R R F S N A T A (SEQ ID NO: 60) | Savinase | RRFAN > E (SEQ ID NO: 94) |
| R R F S N N D E L (SEQ ID NO: 61) | Savinase | K S D |
| K R F A N T E L A (SEQ ID NO: 62) | Savinase | |
| K R F A N T E P A (SEQ ID NO: 63) | Savinase | |
| H E Y D M R V A W (SEQ ID NO: 64) | Lipoprime | EY > M |
| S E Y S M S I T P (SEQ ID NO: 65) | Lipoprime | |
| P E Y T M N A L S (SEQ ID NO: 66) | Lipoprime | |
| L E Y P M S A S Q (SEQ ID NO: 67) | Lipoprime | |
| C S F P L PAP R S C (SEQ ID NO: 68) | Lipoprime | P > PAP > S (SEQ ID NO: 95) |
| C L F PS PAP R S C (SEQ ID NO: 69) | Lipoprime | |
| C D G PAPAP W S C (SEQ ID NO: 70) | Lipoprime | |
| C V Y PS PAP W S C (SEQ ID NO: 71) | Lipoprime | |

TABLE 2-continued

An extract from the epitope-database.

| Sequence alignment | Enzyme | Epitope pattern |
|---|---|---|
| A K I D P K P D (SEQ ID NO: 72) | | AKIDPR (SEQ ID NO: 96) |
| C S V A K I D P R T C (SEQ ID NO: 73) | JE-1 (NATALASE) | K |
| C G S A T I D P R Q C (SEQ ID NO: 74) | JE-1 (NATALASE) | |
| R Y A Q I D P R W (SEQ ID NO: 75) | JE-1 (NATALASE) | |
| C N A D S W G Y P R C (SEQ ID NO: 76) | JE-1 (NATALASE) | ADS > GYP (SEQ ID NO: 97) |
| C D A A S S G Y P L C (SEQ ID NO: 77) | JE-1 (NATALASE) | |
| C D A D D R R Y P R C (SEQ ID NO: 78) | JE-1 (NATALASE) | |
| C N A D N Q M Y P Q C (SEQ ID NO: 79) | JE-1 (NATALASE) | |
| G A A R D A R S A (SEQ ID NO: 80) | Laccase | SRSA (SEQ ID NO: 98) |
| V N H F R K R S A (SEQ ID NO: 81) | PD498 | |
| C S R S A K A R L C G (SEQ ID NO: 82) | Lipoprime | |
| A N P I W S R S A (SEQ ID NO: 83) | Savinase | |
| R K L T L S G R S (SEQ ID NO: 84) | Lipoprime | L > GRSS (SEQ ID NO: 99) |
| G E F N L > G R S S (SEQ ID NO: 85) | JE-1 (NATALASE) | |
| G R F S N S K F K (SEQ ID NO: 86) | Savinase | |

In this example, the epitope S R S A (SEQ ID NO: 98) was found on four different enzymes (laccase, a fungal lipase and two bacterial proteases). Similarly, the epitope L>G R S S (SEQ ID NO: 99) was also found on different parent proteins. This demontrates that proteins of different structure, function and microbial origin may share one or more epitope patterns.

Example 3

Localization of the Respective Epitopes and Epitope Areas on the 3D-structure of Proteins Each epitope was assessed on the 3D-structure of the protein of interest, using an appropriate software (f.e. Swiss Pdb Viewer, WebLite Viewer).

In a first step, the identified epitope patterns were fitted with the 3D-structure of the enzymes. A sequence of at least 3 amino acids, defining a specific epitope pattern, was localized on the 3D-structure of the protein. Conservative mutations (e.g. aspartate for glutamate, lysine for arginine, serine for threonine) were considered as one for those patterns for which phage display had evidenced such exchanges to occur. Among the possible sequences provided by the protein structure, only those were retained where the sequence matched a primary sequence, or where it matched a structural sequence of amino acids, where each amino acid was situated within a distance of 5 Å from the next one. Occasionally, the mobility of the amino acid side chains, as provided by the software program, had to be taken in to consideration for this criterium to be fullfilled. This step gave typically between 0 and 7 possible epitopes per protein.

Secondly, the remaining anchor amino acids as well as the variable amino acids, i.e. amino acids that were not defining a pattern but were present in the individual sequences identified by phage library screening, were assessed in the area around the various amino acid sequences localized in step 1. Only amino acids situated within a distance of 5 Å from the next one were included. This step gave typically between 0 and 3 possible candidates.

Finally, an accessibility criterium was introduced. The criterium was that at least half of the anchor amino acids had a surface that was >30% accessible. Typically, <2 epitopes were retained.

Thus, a number of epitope sequences were identified and localised on the surface of various proteins. As suggested by sequence alignment, structural analysis confirmed most of the epitopes to be enzyme specific, with only few exceptions. Overall, most of the identified epitopes were at least partially structural. However, some proteins (e.g. amylase) expressed predominantly primary sequence epitopes. Typically, the epitopes were localized in very discrete areas of the enzymes, and different epitopes often shared amino acids (hot-spots).

Figure 1A:
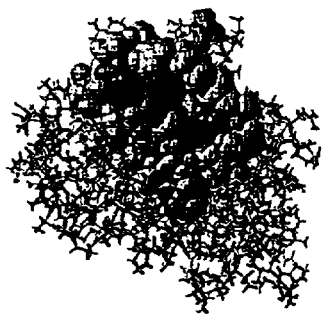
Figure 1B:
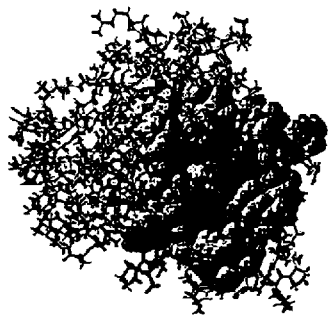
Figure 1B:
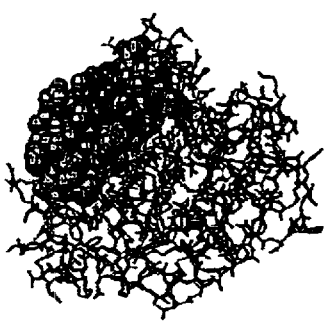

It is common knowledge that amino acids that surround binding sequences can affect binding of a ligand without participating actively in the binding process. Based on this knowledge, areas covered by amino acids with potential steric effects on the epitope-antibody interaction, were defined around the identified epitopes. Practically, all amino acids situated within 5 Å from the amino acids defining the epitope were included. The accessibility criterium was not included as hidden amino acids can have an effect on the surrounding structures. 3D-strctures showing the respective epitopes and epitope areas of different enzymes are shown in FIG. 1.

Example 4

Production, Selection, and Evaluation of Enzyme Variants with Reduced Antigenicity or Immunogenicity Hot-spots or epitopes were mutated using techniques know to the expert in the field (e.g. site-directed mutagenesis, error-prone PCR).

In the examples shown below, variants were made by site-directed mutagenesis. Amino acid exchanges giving new epitopes or duplicating existing epitopes according to the information collected in the epitope-database (See Example 1), were avoided in the mutagenesis process.

Enzyme variants were screened for reduced binding of antibodies raised against the backbone enzyme. This antibody binding was assessed by established. assays (e.g. competitive ELISA, agglutination assay).

Variants with reduced antibody binding capacity were further evaluated in animal studies.

Mice were immunized subcutanuously weekly, for a period of 20 weeks, with 50 μl 0.9% (wt/vol) NaCl (control group), or 50 μl 0.9% (wt/vol) NaCl containing 10 μg of protein. Blood samples (100 μl) were collected from the eye one week after every second immunization. Serum was obtained by blood clotting and centrifugation.

Specific IgG1 and IgE levels were determined using the ELISA specific for mouse or rat IgG1 or IgE. Differences between data sets were analyzed by using appropriate statistical methods.

A. Site-directed Mutagenesis of Amino Acids Defining Epitopes, with an Effect on IgG1 and/or IgE Responses in Mice Epitope: A172/A169 R170 A194 G193 N261
Pattern: A R>R>A>N (SEQ ID NO: 92)
Antibody: IgG1+IgE
Backbone: Savinase
The variant carried mutation R170F.

In a competitive IgE ELISA, this variant was less effective in competing for anti-savinase antibodies, giving a 15% lower endpoint inhibition as compared to the savinase backbone.

Mouse studies revealed an 80% reduction of the specific IgE levels, as compared to savinase backbone (p<0.01). The IgG1 levels were not significantly affected.

Epitope: S216 E219 Y220
Pattern: E Y>M
Antibody: IgG1
Backbone: Lipoprime
The variant carried mutation S216W.

In a competitive IgG ELISA, the variant was less effective in competing for Lipolase antibodies, giving a 38% decrease in endpoint inhibition as compared to the enzyme backbone.

Mouse studies revealed a 69% decrease in specific IgG1 levels, compared to the lipolase backbone (p<0.05). The IgE levels were not significantly affected.

B. Site-directed Mutagenesis of Epitopes, with Examples of Epitope Duplication, and New Epitope Formation, Respectively, Predicted by the Epitope-database Epitope: T143 N173 N140 E136 L135
Pattern: S/T N N>E L (SEQ ID NO: 100)
Antibody: IgG1
Backbone: Savinase
The variant carried mutation E136R.

In a competitive IgG ELISA, the variants was less effective in competing for savinase antibodies, giving a 38% decrease in endpoint inhibition as compared to the savinase backbone.

Mouse studies revealed a dramatic increase in specific IgG1 levels, compared to savinase backbone (p<0.01). The IgE levels were not significantly affected.

Mutation E136R establishes an IgG1 epitope of the R Y P R/K (SEQ ID NO: 101) pattern, previously identified on PD498. Apparently, this new epitope was more antigenic in mice than the existing epitope. The introduction of a savinase unrelated epitope on the savinase backbone could explain the observed discrepancy between competitive ELISA and animal studies.

In this example, it was found that using information derived exclusively from screening phage libraries with anti-PD498 antibodies (to identify the R Y P R/K (SEQ ID NO: 101) epitope pattern of Table 2) one could predict the outcome of a genetic engineering experiment for Savinase in which the E136R mutation created the PD498-epitope on the Savinase surface, leading to increased immunogenicity of this Savinase variant. This demonstrates that the epitope patterns identified may be used to predict the effect on immunogenicity of substitutions in proteins that are different from the parent protein(s) used to identify the epitope pattern.

C. Site-directed Mutagenesis of Amino Acids Defining Epitope Areas, with a Differential Effect on IgG1 and IgE Antibody Levels in Mice, and an Inhibiting Effect on IgG Binding, Respectively Epitope: A172/A169 R170 A194 G193 N261
Pattern: A R>R>A>N (SEQ ID NO: 92)
Antibody: IgG1+IgE
Backbone: Savinase
Epitope area: P131, S132, A133, L135, E136, V139, A151, A152, S153, G161, S162, I165, S166, Y167, P168, Y171, N173, A174, A176, Q191, Y192, G195, L196, R247, S259, T260, L262, Y263, G264.

The variant was different at position Y167 by the mutation Y167I.

In a competitive IgE ELISA, the variant was less effective in competing for anti-savinase antibodies, giving a 8% lower endpoint inhibition as compared to the its backbone.

Mouse studies revealed an 75% reduction of the specific IgE levels, as compared to the backbone (p<0.01). In contrast, the IgG1 levels were dramatically increased (p<0.01).

Epitope: T143 N173 N140 E136 L135
Pattern: S/T N N>E L (SEQ ID NO: 100)
Antibody: IgG1
Backbone: Savinase
Epitope area: V10A, I107, A108, L111, E112, G115, S132, A133, T134, Q137, A138, V139, S141, A142, S144, R145, G146, V147, V149, Y167, P168, Y171, A172, A174, M175, N243, R247.

While variant no. 1 was mutated at the epitope position (N140D), variant no. 2 was mutated at N140 (N140D), but also at the epitope area position (A172D).

In a competitive IgG ELISA, variant no. 1 was less effective in competing for anti-savinase antibodies, as compared with savinase. This variant revealed a 21% lower, endpoint inhibition as compared to the its backbone.

Variant no. 2 resulted in an endpoint inhibition that was 60% lower as. compared to savinase, and 40% as compared with variant no. 1.

Example 5

Conjugation of Savinase Variant E136K with Activated bis-PEG-1000

4.9 mg of the Savinase variant was incubated in 50 mM Sodium Borate pH 9.5 with 12 mg of N-succinimidyl carbonate activated bis-PEG 1000 in a reaction volume of approximately 2 ml. The reaction was carried out at ambient temperature using magnetic stirring while keeping the pH within the interval 9.0–9.5 by addition of 0.5 M NaOH. The reaction time was 2 hours.

The derivatives was purified and reagent excess removed by size exclusion chromatography on a Superdex-75 column (Pharmacia) equilibrated in 50 mM Sodium Borate, 5mM Succinic Acid, 150 mM NaCl, 1 mM CaCl$_2$ pH 6.0.

The conjugate was stored at −20° C., in the above described buffer.

Compared with the parent enzyme variant, the protease. activity of the conjugate was retained (97% using Dimethylcasein as substrate at pH 9).

Example 6

Competitive ELISA was performed according to established procedures. In short, a 96 well ELISA plate was coated with the parent protein. After proper blocking and washing, the coated antigen was incubated with rabbit anti-enzyme polyclonal antiserum in the presence of various amounts of modified protein (the competitor).

The amounts of residual rabbit antiserum was detected by pig anti-rabbit immunoglobulin, horshraddish peroxidase labeled.

Epitope: T143 N173 N140 E136 L135
Pattern: S/T N N>E L (SEQ ID NO: 100)
Antibody: IgG1

Backbone: Savinase

Mutation: E136K

Modification: bis-NHS-PEG1000

Competitive ELISA on the unmodified enzyme of the PEG-ylated derivative. The result is shown in FIG. 2.

The data show that the derivative (60% endpoint inhibition) has reduced capacity to bind enzyme specific immunoglobulins, as compared with the parent protein (100% endpoint inhibition).

What is claimed is:

1. A method of producing a protein variant, comprising the steps of:

(a) subjecting a random peptide display package library to one or more antbodies to identify peptides that bind to the one or more of the antibodies;

(b) identifying one or more epitope patterns by aligning the peptides that bind to the one or more of the antibodies with each other;

(c) obtaining a three-dimensional structure of a parent protein;

(d) identifying the one or more epitope patterns on the three-dimensional structure of the parent protein;

(e) identifying an epitope area of amino acids situated within 5 Å of any amino acid of the one or more epitope patterns of the parent protein; and (f) modifying one or more amino acids identified in step (e) of the parent protein to form the protein variant, wherein the protein variant retains functionality of the parent protein and has a lower immunogenicity than the parent protein.

2. The method of claim 1, wherein the protein variant has a lower allergenicity than the parent protein.

3. The method of claim 1, wherein the one or more antibodies are raised against the parent protein.

4. The method of claim 1, wherein the parent protein is an enzyme.

5. The method of claim 4, wherein the enzyme is a carbohydrase, glycose isomerase, glycosyl hydrolase, lipase, oxidoreductase, peroxidase, phytase, polysaccharide lyase, protease, or transglutaminase.

6. The method of claim 1, wherein the one or more antibodies are IgG or IgE antibodies.

7. The method of claim 1, wherein the peptide display package library is a phage display library.

8. The method of claim 1, wherein the peptides of the peptide display package library are oligopeptides having from 5 to 25 amino acids.

9. The method of claim 1, wherein the epitope area is changed by substituting at least one amino acid of the epitope area.

10. The method of claim 1, wherein the epitope area is changed by adding or deleting at least one amino acid of the epitope area.

11. The method of claim 1, wherein the epitope pattern is changed by substituting at least one amino acid of the epitope pattern.

12. The method of claim 1, wherein the epitope pattern is changed by adding or deleting at least one amino acid of the epitope pattern.

13. The method of claim 1, wherein the epitope area is modified by substituting at least one amino acid with and/or inserting an amino acid which is capable of covalent conjugation to an activated molecule.

14. The method of claim 13, wherein the amino acid which is capable of covalent conjugation to an activated molecule is selected from the group consisting of K, R, C, D, E.

15. The method of claim 13, wherein the molecule for covalent conjugation is an activated synthetic or natural polymer.

16. The method of claim 15, wherein the activated synthetic polymer is a polyethylene glycol.

17. The method of claim 1, wherein the immunogenicity is measured by competitive ELISA.

18. The method of claim 17, wherein the immunogenicity of the protein variant is less than 75% of the immunogenicity of the parent protein.

19. The method of claim 1, further comprising:

(g) culturing a host comprising a DNA sequence encoding the protein variant in a suitable culture medium to obtain expression and secretion of the protein variant; and (h) recovering the protein variant.

20. The method of claim 1, wherein the one or more epitope patterns that are identified on the three-dimensional structure of the parent protein are structural epitopes.

21. The method of claim 1, wherein the one or more epitope patterns that are identified on the three-dimensional structure of the parent protein are linear epitopes.

* * * * *

SEQUENCE LISTING

```
<160> NUMBER OF SEQ ID NOS: 101

<210> SEQ ID NO 1
<211> LENGTH: 9
<212> TYPE: PRT
<213> ORGANISM: Artificial
<220> FEATURE:
<223> OTHER INFORMATION: Synthetic

<400> SEQUENCE: 1

Pro Arg Ser Asp Pro Gly Thr Pro Thr
1               5

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Pro Arg Thr Asp Pro Gly Trp Leu Ala
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Pro Ser Ser Asp Pro Gly Ala Arg Ser
1               5

<210> SEQ ID NO 4
<211> LENGTH: 9
<212> TYPE: PRT
<213> ORGANISM: Artificial
<220> FEATURE:
<223> OTHER INFORMATION: Synthetic

<400> SEQUENCE: 4

Trp Pro Lys Ser Asp Ala Gly Asp Ser
1               5

<210> SEQ ID NO 5
<211> LENGTH: 9
<212> TYPE: PRT
<213> ORGANISM: Artificial
<220> FEATURE:
<223> OTHER INFORMATION: Synthetic

<400> SEQUENCE: 5
```

Gly Pro Ser Arg Asp Ala Gly Leu Leu
1               5

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Gly Pro Ser Arg Asp Ala Gly Leu Leu
1               5

<210> SEQ ID NO 7
<211> LENGTH: 9
<212> TYPE: PRT
<213> ORGANISM: Artificial
<220> FEATURE:
<223> OTHER INFORMATION: Synthetic

<400> SEQUENCE: 7

Gly Ala Ala Arg Asp Ala Arg Ser Ala
1               5

<210> SEQ ID NO 8
<211> LENGTH: 9
<212> TYPE: PRT
<213> ORGANISM: Artificial
<220> FEATURE:
<223> OTHER INFORMATION: Synthetic

<400> SEQUENCE: 8

His Val Phe Asp Lys Asn Val Thr Arg
1               5

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9

Gln Leu Tyr Gly Asp Glu Gln Leu Pro
1               5

<210> SEQ ID NO 10
<211> LENGTH: 9
<212> TYPE: PRT
<213> ORGANISM: Artificial
<220> FEATURE:
<223> OTHER INFORMATION: Synthetic

<400> SEQUENCE: 10

Gly Ser Ala Thr Ile Asp Pro Arg Gln
1               5

<210> SEQ ID NO 11
<211> LENGTH: 9
<212> TYPE: PRT
<213> ORGANISM: Artificial
<220> FEATURE:
<223> OTHER INFORMATION: Synthetic

<400> SEQUENCE: 11

```
His Glu Tyr Pro Met Asp Phe His Leu
1               5

<210> SEQ ID NO 12
<211> LENGTH: 9
<212> TYPE: PRT
<213> ORGANISM: Artificial
<220> FEATURE:
<223> OTHER INFORMATION: Synthetic

<400> SEQUENCE: 12

Ser Glu Tyr Ser Met Ser Ile Thr Pro
1               5

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

Pro Glu Tyr Thr Met Asn Ala Leu Ser
1               5

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Gln Arg Pro Pro Arg Tyr Glu Leu Glu
1               5

<210> SEQ ID NO 15
<211> LENGTH: 9
<212> TYPE: PRT
<213> ORGANISM: Artificial
<220> FEATURE:
<223> OTHER INFORMATION: Synthetic

<400> SEQUENCE: 15

Arg Lys Leu Thr Leu Ser Gly Arg Ser
1               5

<210> SEQ ID NO 16
<211> LENGTH: 9
<212> TYPE: PRT
<213> ORGANISM: Artificial
<220> FEATURE:
<223> OTHER INFORMATION: Synthetic

<400> SEQUENCE: 16

Thr Arg Tyr His Arg Arg Pro Pro Leu
1               5

<210> SEQ ID NO 17
<211> LENGTH: 9
<212> TYPE: PRT
<213> ORGANISM: Artificial
<220> FEATURE:
<223> OTHER INFORMATION: Synthetic

<400> SEQUENCE: 17

Ser Arg Tyr Asn Lys Lys Pro His Leu
```

```
1               5
```

<210> SEQ ID NO 18
<211> LENGTH: 9
<212> TYPE: PRT
<213> ORGANISM: Artificial
<220> FEATURE:
<223> OTHER INFORMATION: Synthetic

<400> SEQUENCE: 18

```
Asn Lys Leu Ala Thr Arg Glu Pro Met
1               5
```

<210> SEQ ID NO 19
<211> LENGTH: 9
<212> TYPE: PRT
<213> ORGANISM: Artificial
<220> FEATURE:
<223> OTHER INFORMATION: Synthetic

<400> SEQUENCE: 19

```
Val Asn His Phe Arg Lys Arg Ser Ala
1               5
```

<210> SEQ ID NO 20
<211> LENGTH: 9
<212> TYPE: PRT
<213> ORGANISM: Artificial
<220> FEATURE:
<223> OTHER INFORMATION: Synthetic

<400> SEQUENCE: 20

```
Arg Gly Leu Ser Met Ile Met Gly Lys
1               5
```

<210> SEQ ID NO 21
<211> LENGTH: 9
<212> TYPE: PRT
<213> ORGANISM: Artificial
<220> FEATURE:
<223> OTHER INFORMATION: Synthetic

<400> SEQUENCE: 21

```
Val His Ala Gly Pro Arg Ala Gly Thr
1               5
```

<210> SEQ ID NO 22
<211> LENGTH: 9
<212> TYPE: PRT
<213> ORGANISM: Artificial
<220> FEATURE:
<223> OTHER INFORMATION: Synthetic

<400> SEQUENCE: 22

```
Val His Ser Gly Pro Arg Ala Gly Tyr
1               5
```

<210> SEQ ID NO 23
<211> LENGTH: 9
<212> TYPE: PRT
<213> ORGANISM: Artificial
<220> FEATURE:
<223> OTHER INFORMATION: Synthetic

<400> SEQUENCE: 23

```
Val His Ala Gly Pro Arg Ala Gly Thr
1               5
```

```
<210> SEQ ID NO 24
<211> LENGTH: 9
<212> TYPE: PRT
<213> ORGANISM: Artificial
<220> FEATURE:
<223> OTHER INFORMATION: Synthetic

<400> SEQUENCE: 24

Val His Ala Gly Pro Arg Ala Gly Thr
1               5

<210> SEQ ID NO 25
<211> LENGTH: 9
<212> TYPE: PRT
<213> ORGANISM: Artificial
<220> FEATURE:
<223> OTHER INFORMATION: Synthetic

<400> SEQUENCE: 25

Val His Ala Gly Pro Arg Ala Gly Thr
1               5

<210> SEQ ID NO 26
<211> LENGTH: 9
<212> TYPE: PRT
<213> ORGANISM: Artificial
<220> FEATURE:
<223> OTHER INFORMATION: Synthetic

<400> SEQUENCE: 26

Val Thr Arg Gly Pro Asn Ala Gly Ser
1               5

<210> SEQ ID NO 27
<211> LENGTH: 9
<212> TYPE: PRT
<213> ORGANISM: Artificial
<220> FEATURE:
<223> OTHER INFORMATION: Synthetic

<400> SEQUENCE: 27

Val His Ala Gly Pro Arg Ala Gly Thr
1               5

<210> SEQ ID NO 28
<211> LENGTH: 9
<212> TYPE: PRT
<213> ORGANISM: Artificial
<220> FEATURE:
<223> OTHER INFORMATION: Synthetic

<400> SEQUENCE: 28

Val His Ser Gly Pro Arg Ala Gly Tyr
1               5

<210> SEQ ID NO 29
<211> LENGTH: 9
<212> TYPE: PRT
<213> ORGANISM: Artificial
<220> FEATURE:
<223> OTHER INFORMATION: Synthetic

<400> SEQUENCE: 29

Val His Ala Gly Pro Arg Ala Gly Thr
1               5
```

```
<210> SEQ ID NO 30
<211> LENGTH: 9
<212> TYPE: PRT
<213> ORGANISM: Artificial
<220> FEATURE:
<223> OTHER INFORMATION: Synthetic

<400> SEQUENCE: 30

Val His Ala Gly Pro Arg Ala Gly Thr
1               5

<210> SEQ ID NO 31
<211> LENGTH: 9
<212> TYPE: PRT
<213> ORGANISM: Artificial
<220> FEATURE:
<223> OTHER INFORMATION: Synthetic

<400> SEQUENCE: 31

Val His Ala Gly Pro Arg Ala Gly Thr
1               5

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Val Thr Arg Gly Pro Asn Ala Gly Ser
1               5

<210> SEQ ID NO 33
<211> LENGTH: 9
<212> TYPE: PRT
<213> ORGANISM: Artificial
<220> FEATURE:
<223> OTHER INFORMATION: Synthetic

<400> SEQUENCE: 33

Leu Ser Gly Pro Leu Ala Gly Arg Val
1               5

<210> SEQ ID NO 34
<211> LENGTH: 9
<212> TYPE: PRT
<213> ORGANISM: Artificial
<220> FEATURE:
<223> OTHER INFORMATION: Synthetic

<400> SEQUENCE: 34

Phe Asn Asp Ala Phe Phe Val Lys Met
1               5

<210> SEQ ID NO 35
<211> LENGTH: 9
<212> TYPE: PRT
<213> ORGANISM: Artificial
<220> FEATURE:
<223> OTHER INFORMATION: Synthetic

<400> SEQUENCE: 35

Thr Phe His Asp Ala Pro Ala Leu Gln
1               5
```

```
<210> SEQ ID NO 36
<211> LENGTH: 9
<212> TYPE: PRT
<213> ORGANISM: Artificial
<220> FEATURE:
<223> OTHER INFORMATION: Synthetic

<400> SEQUENCE: 36

Thr Phe His Asp Ala Pro Ala Leu Gln
1               5

<210> SEQ ID NO 37
<211> LENGTH: 9
<212> TYPE: PRT
<213> ORGANISM: Artificial
<220> FEATURE:
<223> OTHER INFORMATION: Synthetic

<400> SEQUENCE: 37

Asp Phe His Val Lys Tyr Ala Ala Gln
1               5

<210> SEQ ID NO 38
<211> LENGTH: 9
<212> TYPE: PRT
<213> ORGANISM: Artificial
<220> FEATURE:
<223> OTHER INFORMATION: Synthetic

<400> SEQUENCE: 38

Ala Asn Pro Ile Trp Ser Arg Ser Ala
1               5

<210> SEQ ID NO 39
<211> LENGTH: 9
<212> TYPE: PRT
<213> ORGANISM: Artificial
<220> FEATURE:
<223> OTHER INFORMATION: Synthetic

<400> SEQUENCE: 39

Thr Ala Arg Leu Arg Ala Gly Asn Ala
1               5

<210> SEQ ID NO 40
<211> LENGTH: 9
<212> TYPE: PRT
<213> ORGANISM: Artificial
<220> FEATURE:
<223> OTHER INFORMATION: Synthetic

<400> SEQUENCE: 40

Arg Ala Phe Arg Arg Asn Ala Asn Trp
1               5

<210> SEQ ID NO 41
<211> LENGTH: 9
<212> TYPE: PRT
<213> ORGANISM: Artificial
<220> FEATURE:
<223> OTHER INFORMATION: Synthetic

<400> SEQUENCE: 41

Thr Arg Tyr His Arg Arg Pro Pro Leu
1               5

<210> SEQ ID NO 42
```

```
<211> LENGTH: 9
<212> TYPE: PRT
<213> ORGANISM: Artificial
<220> FEATURE:
<223> OTHER INFORMATION: Synthetic

<400> SEQUENCE: 42

Ser Arg Tyr Asn Lys Lys Pro His Leu
1               5

<210> SEQ ID NO 43
<211> LENGTH: 9
<212> TYPE: PRT
<213> ORGANISM: Artificial
<220> FEATURE:
<223> OTHER INFORMATION: Synthetic

<400> SEQUENCE: 43

Arg Arg Tyr Pro Lys Leu Met Pro Pro
1               5

<210> SEQ ID NO 44
<211> LENGTH: 9
<212> TYPE: PRT
<213> ORGANISM: Artificial
<220> FEATURE:
<223> OTHER INFORMATION: Synthetic

<400> SEQUENCE: 44

Arg Arg Tyr Ser Gln Arg Thr Ile Gln
1               5

<210> SEQ ID NO 45
<211> LENGTH: 12
<212> TYPE: PRT
<213> ORGANISM: Artificial
<220> FEATURE:
<223> OTHER INFORMATION: Synthetic

<400> SEQUENCE: 45

Cys Val His Ser Gly Pro Arg Ala Gly Tyr Cys Gly
1               5                   10

<210> SEQ ID NO 46
<211> LENGTH: 12
<212> TYPE: PRT
<213> ORGANISM: Artificial
<220> FEATURE:
<223> OTHER INFORMATION: Synthetic

<400> SEQUENCE: 46

Cys Ile Thr Ser Gly Pro Arg Ala Gly Asn Cys Gly
1               5                   10

<210> SEQ ID NO 47
<211> LENGTH: 12
<212> TYPE: PRT
<213> ORGANISM: Artificial
<220> FEATURE:
<223> OTHER INFORMATION: Synthetic

<400> SEQUENCE: 47

Cys Leu Ser Gly Pro Leu Ala Gly Arg Val Cys Gly
1               5                   10

<210> SEQ ID NO 48
<211> LENGTH: 9
```

```
<212> TYPE: PRT
<213> ORGANISM: Artificial
<220> FEATURE:
<223> OTHER INFORMATION: Synthetic

<400> SEQUENCE: 48

Pro Arg Ser Asp Pro Gly Thr Pro Thr
1               5

<210> SEQ ID NO 49
<211> LENGTH: 9
<212> TYPE: PRT
<213> ORGANISM: Artificial
<220> FEATURE:
<223> OTHER INFORMATION: Synthetic

<400> SEQUENCE: 49

Pro Arg Thr Asp Pro Gly Trp Leu Ala
1               5

<210> SEQ ID NO 50
<211> LENGTH: 9
<212> TYPE: PRT
<213> ORGANISM: Artificial
<220> FEATURE:
<223> OTHER INFORMATION: Synthetic

<400> SEQUENCE: 50

Pro Ser Ser Asp Pro Gly Ala Arg Ser
1               5

<210> SEQ ID NO 51
<211> LENGTH: 8
<212> TYPE: PRT
<213> ORGANISM: Artificial
<220> FEATURE:
<223> OTHER INFORMATION: Synthetic

<400> SEQUENCE: 51

Pro Arg Ser Asp Thr Gly Phe Gly
1               5

<210> SEQ ID NO 52
<211> LENGTH: 9
<212> TYPE: PRT
<213> ORGANISM: Artificial
<220> FEATURE:
<223> OTHER INFORMATION: Synthetic

<400> SEQUENCE: 52

Asp Pro Val Arg Asp Thr Gly Ala Gly
1               5

<210> SEQ ID NO 53
<211> LENGTH: 9
<212> TYPE: PRT
<213> ORGANISM: Artificial
<220> FEATURE:
<223> OTHER INFORMATION: Synthetic

<400> SEQUENCE: 53

Asp Pro Ala Arg Asp Thr Gly Asp Val
1               5

<210> SEQ ID NO 54
<211> LENGTH: 9
<212> TYPE: PRT
```

```
<213> ORGANISM: Artificial
<220> FEATURE:
<223> OTHER INFORMATION: Synthetic

<400> SEQUENCE: 54

Arg Ala Phe Arg Arg Asn Ala Asn Trp
1               5

<210> SEQ ID NO 55
<211> LENGTH: 12
<212> TYPE: PRT
<213> ORGANISM: Artificial
<220> FEATURE:
<223> OTHER INFORMATION: Synthetic

<400> SEQUENCE: 55

Cys Thr Ala Arg Leu Arg Ala Gly Asn Ala Cys Gly
1               5                   10

<210> SEQ ID NO 56
<211> LENGTH: 12
<212> TYPE: PRT
<213> ORGANISM: Artificial
<220> FEATURE:
<223> OTHER INFORMATION: Synthetic

<400> SEQUENCE: 56

Cys Thr Ala Arg Val Val Ala Leu Gly Val Cys Gly
1               5                   10

<210> SEQ ID NO 57
<211> LENGTH: 9
<212> TYPE: PRT
<213> ORGANISM: Artificial
<220> FEATURE:
<223> OTHER INFORMATION: Synthetic

<400> SEQUENCE: 57

Phe Cys Thr Asn Asn Cys Glu Leu Ser
1               5

<210> SEQ ID NO 58
<211> LENGTH: 9
<212> TYPE: PRT
<213> ORGANISM: Artificial
<220> FEATURE:
<223> OTHER INFORMATION: Synthetic

<400> SEQUENCE: 58

Arg Arg Phe Ser Asn Asn Asp Glu Leu
1               5

<210> SEQ ID NO 59
<211> LENGTH: 9
<212> TYPE: PRT
<213> ORGANISM: Artificial
<220> FEATURE:
<223> OTHER INFORMATION: Synthetic

<400> SEQUENCE: 59

Lys Arg Phe Ala Asn Thr Glu Leu Ala
1               5

<210> SEQ ID NO 60
<211> LENGTH: 8
<212> TYPE: PRT
<213> ORGANISM: Artificial
```

```
<220> FEATURE:
<223> OTHER INFORMATION: Synthetic

<400> SEQUENCE: 60

Arg Arg Phe Ser Asn Ala Thr Ala
1               5

<210> SEQ ID NO 61
<211> LENGTH: 9
<212> TYPE: PRT
<213> ORGANISM: Artificial
<220> FEATURE:
<223> OTHER INFORMATION: Synthetic

<400> SEQUENCE: 61

Arg Arg Phe Ser Asn Asn Asp Glu Leu
1               5

<210> SEQ ID NO 62
<211> LENGTH: 9
<212> TYPE: PRT
<213> ORGANISM: Artificial
<220> FEATURE:
<223> OTHER INFORMATION: Synthetic

<400> SEQUENCE: 62

Lys Arg Phe Ala Asn Thr Glu Leu Ala
1               5

<210> SEQ ID NO 63
<211> LENGTH: 9
<212> TYPE: PRT
<213> ORGANISM: Artificial
<220> FEATURE:
<223> OTHER INFORMATION: Synthetic

<400> SEQUENCE: 63

Lys Arg Phe Ala Asn Thr Glu Pro Ala
1               5

<210> SEQ ID NO 64
<211> LENGTH: 9
<212> TYPE: PRT
<213> ORGANISM: Artificial
<220> FEATURE:
<223> OTHER INFORMATION: Synthetic

<400> SEQUENCE: 64

His Glu Tyr Asp Met Arg Val Ala Trp
1               5

<210> SEQ ID NO 65
<211> LENGTH: 9
<212> TYPE: PRT
<213> ORGANISM: Artificial
<220> FEATURE:
<223> OTHER INFORMATION: Synthetic

<400> SEQUENCE: 65

Ser Glu Tyr Ser Met Ser Ile Thr Pro
1               5

<210> SEQ ID NO 66
<211> LENGTH: 9
<212> TYPE: PRT
<213> ORGANISM: Artificial
<220> FEATURE:
```

<223> OTHER INFORMATION: Synthetic

<400> SEQUENCE: 66

Pro Glu Tyr Thr Met Asn Ala Leu Ser
1               5

<210> SEQ ID NO 67
<211> LENGTH: 9
<212> TYPE: PRT
<213> ORGANISM: Artificial
<220> FEATURE:
<223> OTHER INFORMATION: Synthetic

<400> SEQUENCE: 67

Leu Glu Tyr Pro Met Ser Ala Ser Gln
1               5

<210> SEQ ID NO 68
<211> LENGTH: 11
<212> TYPE: PRT
<213> ORGANISM: Artificial
<220> FEATURE:
<223> OTHER INFORMATION: Synthetic

<400> SEQUENCE: 68

Cys Ser Phe Pro Leu Pro Ala Pro Arg Ser Cys
1               5                   10

<210> SEQ ID NO 69
<211> LENGTH: 11
<212> TYPE: PRT
<213> ORGANISM: Artificial
<220> FEATURE:
<223> OTHER INFORMATION: Synthetic

<400> SEQUENCE: 69

Cys Leu Phe Pro Ser Pro Ala Pro Arg Ser Cys
1               5                   10

<210> SEQ ID NO 70
<211> LENGTH: 11
<212> TYPE: PRT
<213> ORGANISM: Artificial
<220> FEATURE:
<223> OTHER INFORMATION: Synthetic

<400> SEQUENCE: 70

Cys Asp Gly Pro Ala Pro Ala Pro Trp Ser Cys
1               5                   10

<210> SEQ ID NO 71
<211> LENGTH: 11
<212> TYPE: PRT
<213> ORGANISM: Artificial
<220> FEATURE:
<223> OTHER INFORMATION: Synthetic

<400> SEQUENCE: 71

Cys Val Tyr Pro Ser Pro Ala Pro Trp Ser Cys
1               5                   10

<210> SEQ ID NO 72
<211> LENGTH: 8
<212> TYPE: PRT
<213> ORGANISM: Artificial
<220> FEATURE:
<223> OTHER INFORMATION: Synthetic

```
<400> SEQUENCE: 72

Ala Lys Ile Asp Pro Lys Pro Asp
1               5

<210> SEQ ID NO 73
<211> LENGTH: 11
<212> TYPE: PRT
<213> ORGANISM: Artificial
<220> FEATURE:
<223> OTHER INFORMATION: Synthetic

<400> SEQUENCE: 73

Cys Ser Val Ala Lys Ile Asp Pro Arg Thr Cys
1               5                   10

<210> SEQ ID NO 74
<211> LENGTH: 11
<212> TYPE: PRT
<213> ORGANISM: Artificial
<220> FEATURE:
<223> OTHER INFORMATION: Synthetic

<400> SEQUENCE: 74

Cys Gly Ser Ala Thr Ile Asp Pro Arg Gln Cys
1               5                   10

<210> SEQ ID NO 75
<211> LENGTH: 9
<212> TYPE: PRT
<213> ORGANISM: Artificial
<220> FEATURE:
<223> OTHER INFORMATION: Synthetic

<400> SEQUENCE: 75

Arg Tyr Ala Gln Ile Asp Pro Arg Trp
1               5

<210> SEQ ID NO 76
<211> LENGTH: 11
<212> TYPE: PRT
<213> ORGANISM: Artificial
<220> FEATURE:
<223> OTHER INFORMATION: Synthetic

<400> SEQUENCE: 76

Cys Asn Ala Asp Ser Trp Gly Tyr Pro Arg Cys
1               5                   10

<210> SEQ ID NO 77
<211> LENGTH: 11
<212> TYPE: PRT
<213> ORGANISM: Artificial
<220> FEATURE:
<223> OTHER INFORMATION: Synthetic

<400> SEQUENCE: 77

Cys Asp Ala Ala Ser Ser Gly Tyr Pro Leu Cys
1               5                   10

<210> SEQ ID NO 78
<211> LENGTH: 11
<212> TYPE: PRT
<213> ORGANISM: Artificial
<220> FEATURE:
<223> OTHER INFORMATION: Synthetic
```

```
<400> SEQUENCE: 78

Cys Asp Ala Asp Asp Arg Arg Tyr Pro Arg Cys
1               5                   10

<210> SEQ ID NO 79
<211> LENGTH: 11
<212> TYPE: PRT
<213> ORGANISM: Artificial
<220> FEATURE:
<223> OTHER INFORMATION: Synthetic

<400> SEQUENCE: 79

Cys Asn Ala Asp Asn Gln Met Tyr Pro Gln Cys
1               5                   10

<210> SEQ ID NO 80
<211> LENGTH: 9
<212> TYPE: PRT
<213> ORGANISM: Artificial
<220> FEATURE:
<223> OTHER INFORMATION: Synthetic

<400> SEQUENCE: 80

Gly Ala Ala Arg Asp Ala Arg Ser Ala
1               5

<210> SEQ ID NO 81
<211> LENGTH: 9
<212> TYPE: PRT
<213> ORGANISM: Artificial
<220> FEATURE:
<223> OTHER INFORMATION: Synthetic

<400> SEQUENCE: 81

Val Asn His Phe Arg Lys Arg Ser Ala
1               5

<210> SEQ ID NO 82
<211> LENGTH: 21
<212> TYPE: PRT
<213> ORGANISM: Artificial
<220> FEATURE:
<223> OTHER INFORMATION: Synthetic

<400> SEQUENCE: 82

Cys Ser Arg Ser Ala Lys Ala Arg Leu Cys Cys Ser Arg Ser Ala Lys
1               5                   10                  15

Ala Arg Leu Cys Gly
            20

<210> SEQ ID NO 83
<211> LENGTH: 9
<212> TYPE: PRT
<213> ORGANISM: Artificial
<220> FEATURE:
<223> OTHER INFORMATION: Synthetic

<400> SEQUENCE: 83

Ala Asn Pro Ile Trp Ser Arg Ser Ala
1               5

<210> SEQ ID NO 84
<211> LENGTH: 9
<212> TYPE: PRT
<213> ORGANISM: Artificial
<220> FEATURE:
```

```
<223> OTHER INFORMATION: Synthetic

<400> SEQUENCE: 84

Arg Lys Leu Thr Leu Ser Gly Arg Ser
1               5

<210> SEQ ID NO 85
<211> LENGTH: 9
<212> TYPE: PRT
<213> ORGANISM: Artificial
<220> FEATURE:
<223> OTHER INFORMATION: Synthetic

<400> SEQUENCE: 85

Gly Glu Phe Asn Leu Gly Arg Ser Ser
1               5

<210> SEQ ID NO 86
<211> LENGTH: 9
<212> TYPE: PRT
<213> ORGANISM: Artificial
<220> FEATURE:
<223> OTHER INFORMATION: Synthetic

<400> SEQUENCE: 86

Gly Arg Phe Ser Asn Ser Lys Phe Lys
1               5

<210> SEQ ID NO 87
<211> LENGTH: 6
<212> TYPE: PRT
<213> ORGANISM: Artificial
<220> FEATURE:
<223> OTHER INFORMATION: Synthetic

<400> SEQUENCE: 87

Ala Ala Pro Phe Asn Pro
1               5

<210> SEQ ID NO 88
<211> LENGTH: 4
<212> TYPE: PRT
<213> ORGANISM: Artificial
<220> FEATURE:
<223> OTHER INFORMATION: Synthetic

<400> SEQUENCE: 88

Arg Tyr Pro Arg
1

<210> SEQ ID NO 89
<211> LENGTH: 7
<212> TYPE: PRT
<213> ORGANISM: Artificial
<220> FEATURE:
<223> OTHER INFORMATION: Synthetic

<400> SEQUENCE: 89

Lys Ser Gly Pro Arg Ala Gly
1               5

<210> SEQ ID NO 90
<211> LENGTH: 7
<212> TYPE: PRT
<213> ORGANISM: Artificial
<220> FEATURE:
<223> OTHER INFORMATION: Synthetic
```

<400> SEQUENCE: 90

Thr Pro Arg Ser Asp Pro Gly
1               5

<210> SEQ ID NO 91
<211> LENGTH: 7
<212> TYPE: PRT
<213> ORGANISM: Artificial
<220> FEATURE:
<223> OTHER INFORMATION: Synthetic

<400> SEQUENCE: 91

Lys Asp Pro Arg Asp Thr Gly
1               5

<210> SEQ ID NO 92
<211> LENGTH: 5
<212> TYPE: PRT
<213> ORGANISM: Artificial
<220> FEATURE:
<223> OTHER INFORMATION: Synthetic

<400> SEQUENCE: 92

Ala Arg Arg Ala Asn
1               5

<210> SEQ ID NO 93
<211> LENGTH: 4
<212> TYPE: PRT
<213> ORGANISM: Artificial
<220> FEATURE:
<223> OTHER INFORMATION: Synthetic

<400> SEQUENCE: 93

Asn Asn Glu Leu
1

<210> SEQ ID NO 94
<211> LENGTH: 6
<212> TYPE: PRT
<213> ORGANISM: Artificial
<220> FEATURE:
<223> OTHER INFORMATION: Synthetic

<400> SEQUENCE: 94

Arg Arg Phe Ala Asn Glu
1               5

<210> SEQ ID NO 95
<211> LENGTH: 11
<212> TYPE: PRT
<213> ORGANISM: Artificial
<220> FEATURE:
<223> OTHER INFORMATION: Synthetic

<400> SEQUENCE: 95

Lys Ser Asp Glu Tyr Met Pro Pro Ala Pro Ser
1               5                   10

<210> SEQ ID NO 96
<211> LENGTH: 6
<212> TYPE: PRT
<213> ORGANISM: Artificial
<220> FEATURE:
<223> OTHER INFORMATION: Synthetic

```
<400> SEQUENCE: 96

Ala Lys Ile Asp Pro Arg
1               5

<210> SEQ ID NO 97
<211> LENGTH: 7
<212> TYPE: PRT
<213> ORGANISM: Artificial
<220> FEATURE:
<223> OTHER INFORMATION: Synthetic

<400> SEQUENCE: 97

Lys Ala Asp Ser Gly Tyr Pro
1               5

<210> SEQ ID NO 98
<211> LENGTH: 4
<212> TYPE: PRT
<213> ORGANISM: Artificial
<220> FEATURE:
<223> OTHER INFORMATION: Synthetic

<400> SEQUENCE: 98

Ser Arg Ser Ala
1

<210> SEQ ID NO 99
<211> LENGTH: 5
<212> TYPE: PRT
<213> ORGANISM: Artificial
<220> FEATURE:
<223> OTHER INFORMATION: Synthetic

<400> SEQUENCE: 99

Leu Gly Arg Ser Ser
1               5

<210> SEQ ID NO 100
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: Misc_feature
<222> LOCATION: (1)..(1)
<223> OTHER INFORMATION: Xaa denotesd Ser or Thr

<400> SEQUENCE: 100

Xaa Asn Asn Glu Leu
1               5

<210> SEQ ID NO 101
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa denotes Arg or Lys

<400> SEQUENCE: 101

Arg Tyr Pro Xaa
1
```